United States Patent [19]

Weinhardt et al.

[11] 4,261,995

[45] Apr. 14, 1981

[54] 4-PHENYL-AND 5-PHENYL-1,4,5,6-TETRAHYDROPYRIMIDINE DERIVATIVES

[75] Inventors: Klaus Weinhardt, Redwood City; Michael Marx, Sunnyvale, both of Calif.

[73] Assignee: Syntex (U.S.A.) Inc., Palo Alto, Calif.

[21] Appl. No.: 71,442

[22] Filed: Aug. 31, 1979

[51] Int. Cl.$^3$ .................. A61K 31/505; C07D 239/14; C07D 239/16
[52] U.S. Cl. .................................... 424/251; 544/330; 544/332
[58] Field of Search ................ 544/330, 332; 424/251

[56] References Cited

U.S. PATENT DOCUMENTS

| 3,655,895 | 4/1972 | Lucas et al. ......................... 544/332 |
| 3,822,262 | 7/1974 | Bream et al. ........................ 544/332 |
| 4,088,771 | 5/1978 | Roszkowski et al. ........... 424/273 R |
| 4,129,661 | 12/1978 | Roszkowski et al. ................ 548/315 |

Primary Examiner—Paul M. Coughlan, Jr.
Attorney, Agent, or Firm—Kate H. Murashige; Tom M. Moran

[57] ABSTRACT

Certain 1,4,5,6-tetrahydropyrimidine compounds which are substituted with an amino, amido or carbamate at the 2-position, with an optionally substituted phenyl at the 5-position or at the 4-position when there is no alkyl at the 1-position and optionally a lower alkyl at the 1-position when the phenyl is at the 5-position are useful as CNS agents and as antihypertensives.

59 Claims, No Drawings

4-PHENYL-AND 5-PHENYL-1,4,5,6-TETRAHYDROPYRIMIDINE DERIVATIVES

BACKGROUND OF THE INVENTION

1. Field of the Invention

This invention relates to 1,4,5,6-tetrahydropyrimidines which are substituted at the 4 or 5 position with a phenyl or substituted phenyl and at the 2 position with an amino, alkylcarbonylamino or alkoxycarbonylamino and the pharmaceutically acceptable salts thereof. The compounds can be combined with suitable pharmaceutical excipients to prepare pharmaceutical compositions which are useful for treating disorders of the central nervous system or cardiovascular system. The invention further relates to methods of preparing the compounds of the invention.

2. Prior Art

A general discussion of psychotic disorders and the use of psychotroptic drugs can be found in the Pharmacological Basis of Therapeutics, 4th Edition, L. S. Goodman and A. Gilman, Editors, McMillan Company, New York (1970).

It is known that certain 2-amino-4-aryl-2-imidazolines show antihypertensive activity. (See Journal of Medicinal Chemistry, Vol. 16, No. 8, p. 901 (1973)). It is also known that certain 4,5-dihydro-5-phenyl-2-lower alkoxycarbonylaminoimidazoles, the substituted phenyl derivatives thereof, and the n-alkyl derivatives are useful for treating disorders of the central nervous system. See for example U.S. Pat. No. 4,088,771 to Roszkowski et al and U.S. Pat. No. 4,129,661 to Roszkowski, et al.

U.S. Pat. Nos. 3,895,112 and 3,707,560 both to DeAngelis and Hess disclose 4-amino-6-aryl-pyrimidines which are useful as muscle relaxants, bronchodilators, and/or platelet aggregation inhibitors. Also, U.S. Pat. No. 2,735,225 to Goodhue and Mahan of Phillips Petroleum describes certain pyrimidines, for example, 4-phthalimido-2,6-dimethylpyrimidine, which are useful as plant growth regulators. It is also known that certain tetrahydropyrimidines, such as 1-methyl-2-(2-thienylethenyl)-tetrahydropyrimidine, are useful as anthelmintic agents used in veterinary practice. See, for example, *Organic Chemistry of Drug Synthesis*, Lednicer and Uitscher, pp. 266–267, John Wiley and Sons (1977).

An entirely new group of tetraphydropyrimidines has now been discovered which is useful in the treatment of disorders of the central nervous system and/or the cardiovascular system.

SUMMARY OF THE INVENTION

The compounds of the invention are represented by the formula

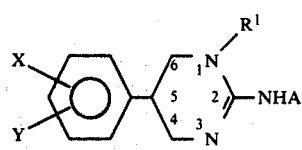

wherein
A is hydrogen, RC(O)— or ROC(O)—;
R is alkyl of one through six carbon atoms;
$R^1$ is hydrogen or alkyl of one through six carbon atoms;
X is hydrogen, fluoro, chloro, bromo, iodo, alkoxy of one through four carbon atoms, benzyloxy, hydroxy, alkyl of one through four carbon atoms, alkylthio of one through four carbon atoms, alkyl sulfinyl of one through four carbon atoms, alkyl sulfonyl of one through four carbon atoms, trifluoromethyl or hydrogen;
Y is hydrogen or is the same as X, and
the phenyl substituent carrying the X and Y is at the 4 or 5 position of the tetrahydropyrimidine ring when $R^1$ is hydrogen or is at the 5-position when $R^1$ is alkyl.

Pharmaceutically acceptable salts of the above compounds are also encompassed within the scope of the invention.

Another aspect of the invention is a pharmaceutical composition which comprises a compound chosen from those represented by Formula I or a pharmaceutically acceptable salt thereof along with a suitable pharmaceutical excepient.

Still another aspect of the invention is the administration of a compound of the invention to an animal to treat disorders of the central nervous system, for example, depression, anxiety, convulsions, centrally induced skeletal muscle spasm and spasticity, or disorders of the cardiovascular system, that is, use as an antihypertensive.

The invention further relates to a process of preparing the compounds of the invention represented by Formula (I) by converting the appropriate, substituted diamine to the 2-amino-4-phenyl (or 5-phenyl)-1,4,5,6-tetrahydropyrimidine. This, in turn, can be converted to the corresponding 2-alkoxycarbonylamino compound or the 2-alkylcarbonylamino compound. Alternatively, the diamine can be converted directly to the 2-alkoxycarbonylamino compound.

A more complete discussion of the preferred embodiments is found hereinafter.

FURTHER DESCRIPTION AND PRESENTLY PREFERRED EMBODIMENTS COMPOUNDS

The broadest aspect of this invention is a compound selected from those represented by the formula

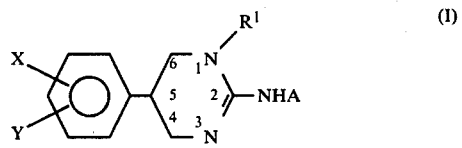

wherein
A is hydrogen, RC(O)— or ROC(O)—;
R is alkyl of one through six carbon atoms;
$R^1$ is hydrogen or alkyl of one through six carbon atoms;
X is fluoro, chloro, bromo, iodo, alkoxy of one through four carbon atoms, benzyloxy, hydroxy, alkyl of one through four carbon atoms, alkylthio of one through four carbon atoms, alkyl sulfinyl of one through four carbon atoms, alkyl sulfonyl of one through four carbon atoms, trifluoromethyl or hydrogen;
Y is hydrogen or is the same as X;
the phenyl substituent carrying the X and Y is at the 4- or 5-position of the tetrahydropyrimidine ring when $R^1$ is hydrogen or is at the 5-position, when $R^1$ is alkyl;
and the pharmaceutically acceptable salts thereof.

A subgroup of this invention includes the compounds represented by Formula (I) wherein A is hydrogen, RC(O)— or ROC(O)—;
R is methyl or ethyl;
$R^1$ is hydrogen, methyl or ethyl;
X is hydrogen, fluoro, chloro, methoxy, ethoxy, methyl, ethyl or hydroxy;
Y is hydrogen or the same as X; and
the pharmaceutically acceptable salts thereof.

The broadest aspect of the invention can be further subdivided into subgroups such as amines, as shown in Formula (II), amides as shown in Formula (III), or carbamates as shown in Formula (IV).

The amines of this invention include the group compounds represented by the formula

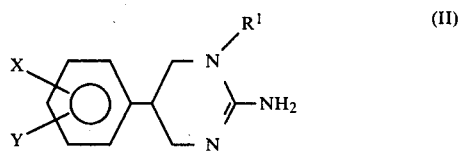

wherein
X is fluoro, chloro, bromo, iodo, alkoxy of one through four carbons atoms, benzyloxy, hydroxy, alkyl of one through four carbon atoms, alkylthio of one through four carbon atoms, alkyl sulfinyl of one through four carbon atoms, alkyl sulfonyl of one through four carbon atoms, trifluoromethyl or hydrogen;
Y is hydrogen or is the same as X;
$R^1$ is hydrogen or alkyl of one through six carbon atoms;
the phenyl substituent carrying the X and Y is at the 4- or 5-position of the tetrahydropyrimidine ring when $R^1$ is hydrogen or is at the 5-position when $R^1$ is alkyl;

A preferred subgroup of this class of compounds includes the compounds represented by Formula (II) wherein X is fluoro, chloro, methoxy, ethoxy, hydroxy, methyl, ethyl or hydrogen; Y is hydrogen or is same as X; and $R^1$ is hydrogen, methyl or ethyl. Of the preferred subgroup, the compounds wherein X is fluoro, chloro or hydrogen; Y is hydrogen or the same as X; and $R^1$ is hydrogen or methyl are particularly preferred.

Typical specific illustrations of the amines of this invention are set forth in the Examples hereafter.

The amides of this invention include the compounds represented by the formula

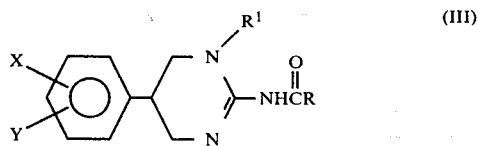

wherein
X is fluoro, chloro, bromo, iodo, alkoxy of one through four carbon atoms, benzyloxy, hydroxy, alkyl of one through four carbon atoms, alkylthio of one through four carbon atoms, alkylsulfinyl of one through four carbon atoms, alkylsulfonyl of one through four carbon atoms, trifluoromethyl or hydrogen;
Y is hydrogen or is the same as X;
R is alkyl of one through six carbon atoms;
$R^1$ is hydrogen or alkyl of one through six carbon atoms; and
the phenyl substituent carrying the X and Y is at the 4- or 5-position of the tetrahydropyrimidine ring when $R^1$ is hydrogen or is at the 5-position, when $R^1$ is alkyl;

A preferred subgroup of this group of compounds includes those represented by Formula (III) wherein X is fluoro, chloro, methoxy, ethoxy, hydroxy, methyl, ethyl or hydrogen; Y is hydrogen or is the same as X; R is methyl or ethyl; and $R^1$ is hydrogen, methyl or ethyl.

Of the preferred subgroup, those compounds particularly preferred include the compounds of Formula (III) wherein X is fluoro, chloro or hydrogen; Y is hydrogen or is the same as X; $R^1$ is hydrogen or methyl and R is methyl.

Typical specific illustrations of the amides of this invention are set forth in the Examples hereafter.

The carbamates of this invention are represented by the compounds of the Formula

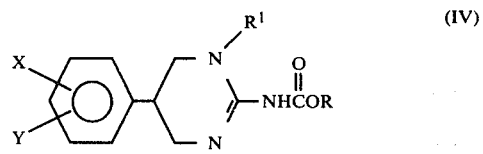

wherein
X is fluoro, chloro, bromo, iodo, alkoxy of one through four carbon atoms, benzyloxy, hydroxy, alkylthio of one through four carbon atoms, alkylsulfinyl of one through four carbon atoms, alkylsulfonyl of one through four carbon atoms, trifluoromethyl or hydrogen;
Y is hydrogen or is the same as X;
R is alkyl of one through six carbon atoms,
$R^1$ is hydrogen or alkyl of one through six carbon atoms; and
the phenyl substituent carrying the X and Y is at the 4- or 5-position of the tetrahydropyrimidine ring when $R^1$ is hydrogen or is at the 5-position, when $R^1$ is alkyl.

A preferred subgroup of this group of compounds includes those represented by Formula (IV) wherein X is fluoro, chloro, methoxy, ethoxy, hydroxy, methyl, ethyl or hydrogen; Y is hydrogen or is the same as X; $R^1$ is hydrogen, methyl or ethyl; and R is methyl or ethyl. Of this subgroup, those particularly preferred are the compounds represented by Formula (IV), wherein X is fluoro, chloro, methoxy, ethoxy, methyl, ethyl or hydrogen; Y is hydrogen or is the same as X; $R^1$ is hydrogen, methyl or ethyl; and R is methyl or ethyl.

Typical specific illustrations of the carbamates of this invention are set forth in the Examples hereafter.

The compounds of this invention are optionally substituted at the 1-position of the tetrahydropyrimidine ring with an alkyl group; at the 2-position with an amino ($-NH_2$), an alkyl carbonylamino (—NHC(O)R) or alkoxycarbonylamino (—NHC(O)OR); and at the 4- or 5-position with a phenyl or substituted phenyl. Where the phenyl substitution is at the 5-position with no substitution at the 1-position, the compounds are not optically active because of tautomerism, i.e. there is an equilibrium between the two linkage isomers. However, once the position of the double bond is fixed by the alkyl substitution at the 1-position, the compounds are optically active due to the asymmetrical atom at the five position. If on the other hand, the phenyl is substituted at the 4-position, the compounds of the invention have an asymmetric carbon atom at the 4-position of the tetrahydropyrimidine ring and thus exist as optically active enantiomers, i.e. (+) and (−) compounds. The above Formulas (I), (II), (III) and (IV) are intended to represent the respective individual (+) and (−) optical enantiomers as well as mixtures thereof, and accordingly the individual enantiomers as well as mixtures thereof (e.g. racemic mixtures) are encompassed within the scope of the invention.

The compounds of the invention will be named herein, for purposes of convenience, as follows:

A. 4-phenyl substituted compounds
2-amino-4-(substituted phenyl)-1,4,5,6-tetrahydropyrimidine;
2-alkylcarbonylamino-4-(substituted phenyl)-1,4,5,6-tetrahydropyrimidine;
2-alkoxycarbonylamino-4-(substituted phenyl)-1,4,5,6-tetrahydropyrimidine;

B. 5-phenyl substituted compounds
2-amino-5-(substituted phenyl)-1,4,5,6-tetrahydropyrimidine;
1-alkyl-2-amino-5-(substituted phenyl)1,4,5,6-tetrahydropyrimidine;
2-alkylcarbonylamino-5-(substituted phenyl)-1,4,5,6-tetrahydropyrimidine;
1-alkyl-2-alkylcarbonylamino-5-(substituted phenyl)-1,4,5,6-tetrahydropyrimidine;
2-alkoxycarbonylamino-5-(substituted phenyl)-1,4,5,6-tetrahydropyrimidine;
1-alkyl-2-alkoxycarbonylamino-5-(substituted phenyl)-1,4,5,6-tetrahydropyrimidine;

Also included within the scope of the invention are pharmaceutically acceptable salts of each of the above subgroups compounds.

Pharmaceutically acceptable salts include those salts of the parent compound which do not significantly adversely affect the pharmaceutical properties (e.g. toxicity, effectiveness, etc.) of the parent compound and are conventionally used in the pharmaceutical art. The pharmaceutically acceptable salts of the present invention are pharmaceutically acceptable hydrogen-anion addition salts of the compounds of Formula (I), (II), (III) and (IV). Suitable pharmaceutically acceptable hydrogen-anion addition salts include (expressed with respect to the anion), for example, inorganic salts such as, for example, chloride, bromide, iodide, sulfate, phosphate, nitrate, and the like, or organic salts such as, for example, acetate, benzoate, lactate, propionate, butyrate, valerate, tartrate, maleate, fumarate, citrate, succinate, tosylate, ascorbate, palmitate, glyconate, adipate, and the like.

The preferred pharmaceutically acceptable salts are the hydrochloride, hydrobromide, nitrate, maleate and citrate, and correspondingly the preferred and particularly preferred salts are the corresponding salts of the groups of the preferred and particularly preferred compounds described above.

Utility and Administration

The compounds of the invention are useful as agents for treating, palliating, or preventing undesirable conditions, in mammals, involving the central nervous system such as depression, anxiety, convulsions, centrally induced skeletal muscle spasms or spasticity disorders. Thus, the compounds of the invention are useful as antidepressants, anxiolytic agents, anticonvulsants, antispasmotics, or antispasticity agents.

Initial determination of the spectrum of psychotropic activity, in mammals, for a given compound is obtained by applying routine experimental procedures. Antidepressant activity is initially determined using the methods discussed in Askew, *Life Sciences*, Vol. 2, p. 725 (1963) and Vernier et al, *Fed. Proc.*, Vol. 21, p. 419 (1962). Depressant or tranquilizing activity (antianxiety agent) is initially determined using methods discussed by Irwin in *Animal and Clinical Pharmacological Technique in Drug Evaluation* edited by J. H. Nodine et al, pp. 36–54, Year Book Medical Publishers, Inc., Chicago (1964). For anticonvulsant activity the method used is described by Swinyard, J. of Amer. Phar. Assoc., Scientific Edition, Vol. 38, p. 201 (1949). For centrally acting skeletal muscle relaxant activity based on polysynaptic transmission inhibition (antispasmotic) the method used is set forth in King and Unna, "The Action of Mephenesin and Other Interneuron Depressants on the Brain Stem", J. Pharmacol. Exp. Ther., Vol. 111, p. 293 (1954); Barnett and Fiore, *European Journal of Pharmacology*, Vol. 13, p. 239 (1971); Kamijo and Koelle, *Proceedings of the Society for Experimental Biology and Medicine*, Vol. 88, pp. 565–568 (1955).

The compounds of the invention are also useful in the treatment and palliation of cardiovascular abnormalities in mammals, particularly in the treatment of hypertension in mammals. Thus a therapeutically effective amount for hypertension will be an amount sufficient to lower the blood pressure in the animal being treated.

In general, the dosage will be an amount effective to achieve the desired results. The preferred dosage depends upon the particular subject and disorder being treated and can vary within wide limits such as, for example, between 0.001 and 50 mg. per kg. of body weight per day, preferably between 0.01 and 10 mg/kg. Generally, where the compounds are administered as antidepressants, they can be administered in the same manner as imipramine and preferably are administered at a rate of less than about 10 mg/kg per day and preferably less than 5 mg/kg. Where the compounds are administered as anticonvulsants, they are best administered prophylactically to prevent or reduce the occurrence and/or severity of convulsions in mammals which are subject to convulsions which are etiopathic to the central nervous system. When the compounds of this invention are administered for the treatment of cardiac disorders such as hypertension, dosages (preferably oral) of about from 0.6–6.0 mg. per kg. of body weight are sufficient.

The compounds can be administered orally, rectally or parenterally (for example, by intravenous, intraperitoneally or intramuscular injection). The compounds are typically administered as pharmaceutical compositions comprising at least one compound of the invention and at least one suitable pharmaceutical excipient. Where the compounds are administered parenterally, they will, of course, be administered in liquid dosage forms, whereas when administered orally or rectally, they can be administered in either solid or liquid forms. Typically, the dosage forms comprise the compound and a pharmaceutically acceptable excipient such as a carrier, preferably formulated in unit dosage form to facilitate the simple administration of precise dosages. The dosage form can optionally contain other compatible medicaments and excipients such as preservatives, emulsifying agents and wetting agents and buffering agents. Liquid dosage forms include, for example solutions, suspensions, emulsions, syrups, elixirs, etc. Liquid carriers include, for example, water, saline solution, etc. Solid dosage forms include, for example, tablets, powders, capsules, pills, etc. Suitable solid carriers include, for example, pharmaceutical grades of starch, lactose, sodium saccharin, sodium bisulfite and the like, and conventional suppository carriers, e.g. polyethylene glycol, polysorbate, stearic acid, diglycol stearate, carbowax, etc.

Thus, the compounds may be prepared as pills such as capsules or tablets each having about 10–200 mg per pill.

Definitions

The following terms, as used hereinabove and below, have the following meaning unless expressly stated to the contrary. The term alkyl includes both straight chain and branched chain alkyls having the number of carbon atoms indicated. For example alkyl of one through four carbon atoms include, for example, methyl, ethyl, n-propyl, isopropyl, t-butyl, n-butyl and the like. Alkyl of one through six includes the foregoing as well as amyl, hexyl and the like. The term alkoxy of one through four carbon atoms can be defined as the group OR' wherein R' is alkyl of one through four carbon atoms.

The term "room temperature" or "ambient temperature" refers to about 20° Centigrade and all temperatures and temperature ranges refer to degrees Centigrade. All percents refer to weight percents and the term equivalent mole amount refers to an amount stoichiometrically equivalent to the other reactant in the reaction referred to.

PROCESS OF THE INVENTION

A. 5-Phenyl-1,4,5,6-tetrahydropyrimidines

The symmetrical compounds of this invention, namely, the 5-(optionally substituted phenyl)-1,4,5,6-tetrahydropyrimidines, are prepared by converting a suitable propane diamine of Formula (D) in Reaction Sequence 1 to the 2-aminotetrahydropyrimidine of Formula (II¹), or the carbamate of Formula (IV¹). The aminotetrahydropyrimidine (II¹) is converted to the carbamate (IV¹) or the amide of Formula (III¹).

REACTION SEQUENCE I

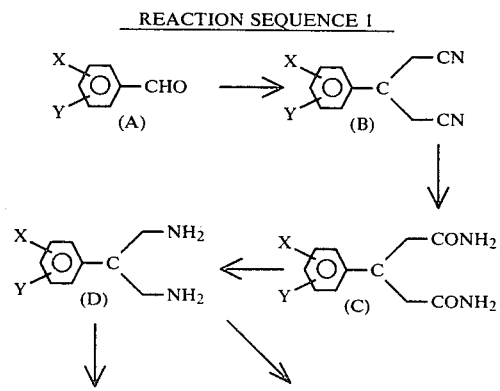

REACTION SEQUENCE I -continued

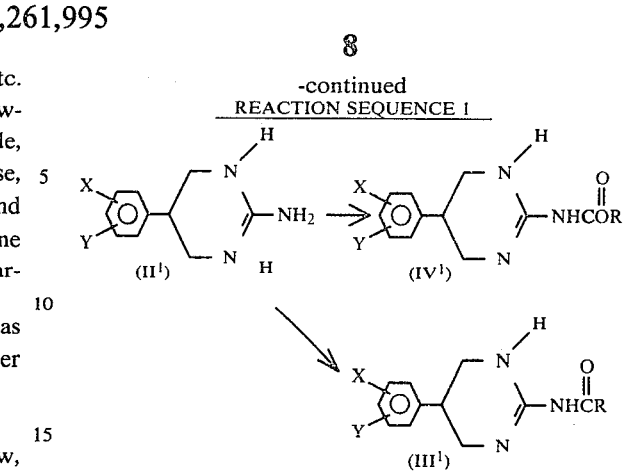

The overall process is set forth in Reaction Sequence 1 using as the starting material an appropriately substituted benzyldehyde of Formula A, where X and Y are as hereinbefore defined. Where X is hydroxy, however it is preferably first converted to benzyloxybenzaldehyde which is reacted as shown in Reaction Sequence 1 and finally the benzyloxy is converted to the hydroxy by hydrogenolysis.

The benzaldehyde Formula (A) is reacted with cyanoacetic acid at a temperature of from about 30° C. to about 120° C. in a suitable solvent. Preferably the temperature is from about 50° C. to about 100° C. The solvent can be any solvent in which the reaction readily takes place but is preferably a cyclic amine such as pyridine. Also present is a small amount of a stronger base such as morpholine, piperidine, piperazine, diazabicyclononine, etc. Preferably this base is piperidine. The cyanoacetic acid reacts with the benzaldehyde according to the principles discussed in Chem. Ber., Vol. 95, pages 195–198, (1962), by Chiemenz and Engelhard. That reference is incorporated herein by reference. The product of this reaction is the corresponding phenylglutaronitrile shown in Reaction Sequence 1 as Formula (B).

The compound of Formula (B) is then treated with an aqueous acid to form the corresponding 3-phenylglutaramide of Formula (C). The acid may be any suitable inorganic mineral acid such as hydrochloric or sulfuric. Preferably sulfuric acid is employed. This reaction can be carried out at temperatures from about 5° C. to about 50° C., but is preferably carried out at about room temperature. Once the reaction is complete, excess acid is neutralized with a suitable base such as ammonium hydroxide and the resulting solid precipitate is collected by filtration, centrifugation or the like. Alternatively, any other known methods of formation of amides from nitriles can be employed. For example, refluxing the nitrile of Formula (B) with aqueous base results in the corresponding amide. The addition of hydrogen peroxide accelerates the hydration of nitriles in alkaline solutions, thus hydrogen peroxide with a suitable base such as sodium carbonate, sodium hydroxide, potassium hydroxide, magnesium hydroxide or the like can be used with success. This is further discussed in Organic Chemistry, 2nd Ed., Cram and Hammond, p. 307, McGraw Hill Book Company, 1964. In addition the process may be performed by adapting the method described by Murray and Cloak in Journal of the American Chemical Society, Vol. 56, pages 2749–2751 (1934). These references are incorporated herein by reference.

The amide of Formula (C) in turn is readily converted into the 2-phenyl-1,3-propanediamine of Formula (D) by adaptation of the Hoffman rearrangement or any of the other known methods for the preparation of amines from amides that proceed with the loss of one carbon, for example, by treatment with lead tetracetate. In the Hoffman rearrangement, the unsubstituted amide is reacted with sodium hypobromite (or aqueous sodium hydroxide and bromine) at low temperatures of $-20°$ to about 10° C. The reaction takes place readily at low temperatures of about $-10°$ to about 10° C. with increased heating as the reaction progresses, the reaction reaching completion at about 50° to 100° C., preferably 70° C. The reaction is discussed in Cram and Hammond's *Organic Chemistry*, ibid, p. 490 and in S. Simons, *J. ORG. CHEM.* 38, 414 (1973). The references are incorporated herein by reference.

Once the diamine of Formula (D) is obtained it can be converted into the 2-amino-1,4,5,6-tetrahydropyrimidine compound or Formula (II$^1$) or the 2-alkoxycarbonylamino-1,4,5,6-tetrahydropyrimidine compound. The 2-amino-5-phenyl-1,4,5,6-tetrahydropyrimidino compounds are prepared by adopting methods known in the art to this particular process. For example, the method set forth in Matier, et al, *J. of MED. CHEM.* 16, No. 8, 901–908 (1973), has been found to be particularly useful. In this case the diamine as the free base is dissolved in a suitable solvent such as methanol and a solution of cyanogen bromide in an inert solvent such as methanol is added to the solution. Generally the reaction will be complete in less than 5 hours at a temperature of about 10° to about 50° C., preferably about 20° to 30° C. This method results in the 2-amino-5-phenyl-1,4,5,6-tetrahydropyrimidine hydrobromide which is then crystallized from a suitable solvent such as methanol and isopropylether.

This compound is readily converted into the amide by reacting with a suitable acid chloride, anhydride, ester or the acid itself in the presence of an activating agent such as dicyclohexylcarbodiimid or carbonyldiimidazole. Alternatively, a carboxylic acid derivative, for example tetraacylglycolrils can be used. For preparations and reactions of tetraacylglycolurils see D. Kuhling, Ann.Chem. 1973, 263 and C. Hase and D. Kuhling, Ann.Chem. 1975, 95.

The 2-alkoxycarbonylamino-5-phenyl-1,4,5,6-tetrahydropyrimidine is readily prepared by adapting known methods to the particular compounds at hand. See for example U.S. Pat. No. 4,088,771 to Roszkowski et al, which is incorporated herein by reference.

The diamine of formula (D) is reacted with a compound represented by the formulas

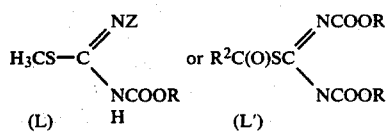

where Z is hydrogen or COOR, R is lower alkyl of one through six carbon atoms and R$^2$ is alkyl of one through five carbon atoms.

This reaction can be conveniently effected by treating the diamine of Formula (D), or typically an acid salt thereof (e.g. the dihydrochloride salt), with the starting material of formula L or L' having the desired R substituent, in a suitable solvent. Typically, the reaction is conducted under alkaline to slightly acid conditions, preferably essentially neutral. Where an acid salt of the diamine of Formula (D) is used, a sufficient amount of an inorganic or organic base is added to the reaction mixture either before or after the addition of one or both of the reactants to neutralize all or part of the acid salt moiety. Suitable bases which can be used include, for example, alkali metal carbonate, or bicarbonates, acetates, for example, sodium carbonate, potassium carbonate, sodium bicarbonate, sodium acetate, alkali metal lower alkoxides, for example, sodium methoxide, potassium methoxide, sodium t-butoxide, lithium methoxide, and the like, alkali metal and alkali earth hydroxides, for example, sodium hydroxide, potassium hydroxide, calcium hydroxide, and the like, and mixtures thereof. Suitable organic bases include, for example, pyridine, triethylamine, diazabicyclononane, and the like or mixtures thereof.

Conveniently, the solvent in which the reaction is carried out is a mixture of water and one or more inert organic solvents. Suitable inert organic solvents which can be used include, for example, methanol, ethanol, isopropanol, diethyl ether, chloroform, benzene and the like and mixtures thereof. The reaction is carried out at temperatures in the range of about from 10° to 100° C., preferably about from 50° to 75° C., for about from ½ hour to 14 days. Typically, a mole ratio of about from 0.5 to 2, preferably about 1 mole of the diamine of Formula (D) is used per mole of starting material of Formula (L) or (L'). However, temperatures, reaction times, and mole ratios both above and below these ranges can be used. Optimum conditions will, of course, vary with the particular reactants and solvents, and can be determined by routine experimentation. The products of Formula (IV) can be separated from the product reaction mixture and further purified by conventional procedures, e.g. filtration, washing, evaporation, crystallization and the like. Non-limiting illustrations of detailed separation and purification procedures can be had by reference to the Examples set forth hereinbelow.

The starting materials of Formulas (L) and (L') are known compounds and can be prepared according to known procedures such as those set forth in Japanese Application No. 50012087 or by obvious modifications of such procedures. The compounds of Formula (C) can be used either as the respective mono- (Z is H) or bis- (Z is COOR) or as a mixture of the mono- and bis-compounds. Conveniently, the compound of Formula (L) is prepared as a mixture of the mono- (Z is H) and bis (Z is COOR) and the mixture then used in the aforedescribed reaction without separation of the mono- and bis-products.

In a further process embodiment, the compounds of the invention represented by Formula (IV$^1$) are prepared by treating the diamine of Formula (D) with a compound of the general formula

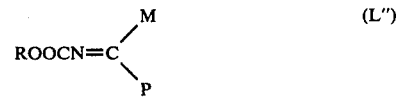

wherein R is as defined hereinabove and M and P independently are chlorine, lower alkoxy or lower alkylthio. The term lower alkoxy or lower alkylthio refers to alkoxy or alkylthio groups having an alkyl group from one through six carbon atoms which may be branched or straight chain attached to an oxygen or sulfur atom.

The reaction preferably is carried out in the presence of a suitable organic or inorganic base, such as triethylamine, pyridine, sodium hydroxide, sodium bicarbonate, or sodium carbonate at 0° to 100° C., preferably at 0° to 50° C.

If one of M or P is halogen and the other of M or P is lower alkoxy or lower alkylthio the reaction is first started in the presence of a base and completed at a pH of 2 to 8 between 0° to 150° C., preferably 20° to 120° C.

If both M and P are lower alkoxy or lower alkylthio, the reaction is carried out at 0° to 150° C., preferably 30° to 120° C., optionally in a solvent such as a lower alkanol, acetonitrile diluted acetic acid, ethylene glycol, tetrahydrofurane, dioxane, benzene, toluene, halogenated hydrocarbon, water, or the like. It is advantageous to use solvents which contain water. The pH range should be between 2 and 8 preferably between 2 and 5.

The compounds of Formula (L″) are known compounds and can be prepared in accordance with the procedures described in German OLS No. 2438120.

In still a further modification the compounds of the invention can be prepared by treating the diamine of Formula (D) with a compound of the general formula

ROOC—NHCN wherein R is as defined above. The reaction conditions are the same as applied with the compounds of the Formula (L″) with M and P both being lower alkoxy or lower alkylthio. These compounds may also be prepared by methods described in German OLS No. 2438120.

In a further embodiment, the compounds of this invention are prepared by reacting the compound of Formula (II′) with a carbonate of the formula

wherein R is alkyl of one through six carbon atoms. This reaction can be conveniently effected at a suitable temperature by treating the compound of formula (II), or typically an acid salt thereof, e.g. the hydrobromide salt, with the carbonate having the desired R substituent in an inert solvent or by using an excess of the carbonate as the solvent. A suitable temperature for the reaction will be about 20° C. to about 120° C., preferably about 70° C. to about 100° C. Typically where an acid salt of compound (II′) is used as the starting material, the salt is treated before addition of the carbonate with a sufficient amount of an inorganic or organic base to liberate the free base. Suitable bases which can be used include, for example, alkali metal carbonates, alkali metal lower alkoxides, for example, sodium methoxide, potassium methoxide, sodium t-butoxide, lithium methoxide, and the like, alkali metal and alkali earth hydroxides, for example sodium hydroxide, potassium hydroxide, calcium hydroxide, and the like, and mixtures thereof. Suitable organic bases include, for example, pyridine, triethylamine, diazabicyclononane, and the like and mixtures thereof. Suitable inert organic solvents which can be used include, for example, toluene, dioxane, and the like and mixtures thereof.

The compounds of the invention can also be prepared by reacting the 2-amine of Formula (II¹) with an alkyl chloroformate (ClCOOR) having the desired R-alkyl substituent in a suitable inert organic solvent; e.g. acetone. This reaction takes place at about −20° C. to about 20° C., preferably about −5° C. to 5° C.

The 5-phenyl-1,4,5,6-tetrahydropyrimidines of this invention which are substituted with an alkyl at the 1-position are prepared from the corresponding N-alkyl-2-phenyl-1,3-propanediamine according to Reaction Sequence 2.

REACTION SEQUENCE 2

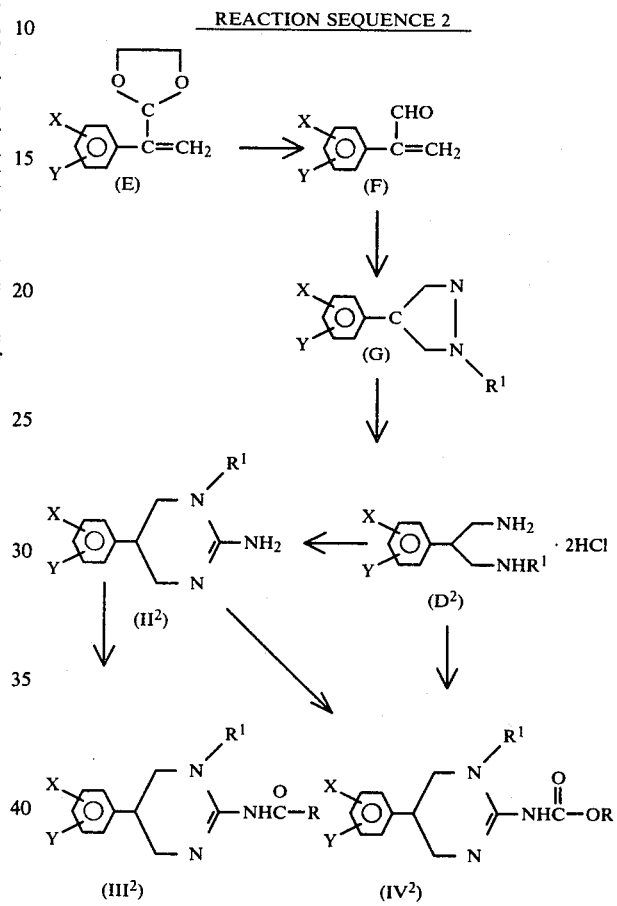

In Reaction Sequence 2, the starting material, ethylene glycol acetal of atropaldehyde of Formula (E) (a known material, see E. Elkik, Bull. Soc. Chim. Fr, 1968(1), 283) is first hydrolyzed by reacting in a weakly acidic aqueous solvent at temperatures of about 25° C. to about 100° C., preferably about 65°-75° C. Any organic or inorganic acid can be used with oxalic acid being preferred. The reaction is carried out in a suitable polar, organic solvent which is miscible with water. The lower alcohols such as methanol, ethanol, isopropanol, and the like are useful, with ethanol being preferred. The hydrolysis can be followed by gas chromatography and is usually complete after about forty minutes at a reaction temperature of 70°-80° C. The liberated atropaldehyde (F) can be isolated (See E. Elkik, supra) or can be reacted in situ by adding an N-alkylhydrazine directly to the hydrolysis mixture. This latter procedure is preferred to avoid the difficulties inherent in the polymerization of atropaldehyde (see E. Elkik, supra). Once the acetal is hydrolyzed a suitable N-alkylhydrazine is added and reacted at temperatures of about 10° C. to about 40° C., preferably ambient temperature. This results in a product represented by Formula (G)

wherein R is alkyl of one through six carbon atoms, depending on the N-alkylhydrazine. For example, N-methylhydrazine, N-ethylhydrazine, N-isopropylhydrazine, N-t-butylhydrazine and N-n-hexylhydrazine results in a compound of Formula (G) wherein R is methyl, ethyl, isopropyl, t-butyl and n-hexyl, respectively. The pyrrazoline of Formula (G) is reduced, for example by catalytic hydrogenation, to the N-alkylpropane diamine of Formula ($D^2$). The compound of Formula ($D^2$) is then converted to the amino pyrimidine ($II^2$), amide ($III^2$) or carbamate ($IV^2$) according to procedures discussed hereinbefore.

B. 4-Phenyl-1,4,5,6-tetrahydropyrimidines

The preparation of the 2-amino-, 2-amido- or 2-alkoxycarbonylamino-4-(optionally substituted phenyl)-1,4,5,6-tetrahydro- pyrimidines is shown in Reaction Sequence 3.

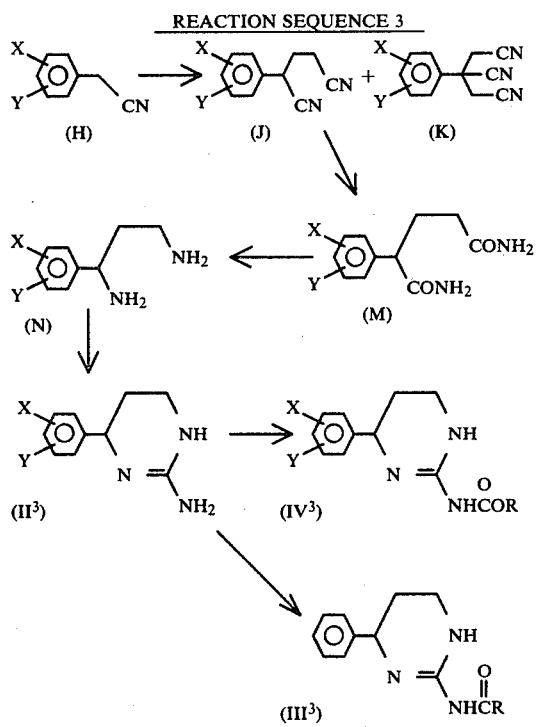

In this case the starting materials represented by Formula (H) are different but the intermediate steps from the phenylglutaranitrile of Formula (J) are similar to those set forth hereinbefore for the 5-phenyl-1,4,5,6-tetrahydropyrimidines and the reaction conditions for those steps as previously defined apply here. The preparation of the compound of Formula (J) occurs as discussed by R. Bertocchio and J. Dreux, Bull. Soc. Chem. Fr. 1962, 1809–1813. In the preparation of the 2-phenylglutaronitrile of Formula (J) the appropriate phenylacetonitrile of Formula (H) is reacted with acrylonitrile ($CH_2=CHCN$) at temperatures of about 30° to 100° C., preferably under reflux for less than 5 hours. Generally, the phenylacetonitrile will be in substantial molar excess over the acrylonitrile and will act as a solvent for the reaction mixture. However, other solvents which are suitable and inert towards the reaction can be used such as toluene. The mixture that results consists mainly of unreacted phenylacetonitrile (H), phenylglutaronitrile (J) and the pentane tricarbonitrile (K). The three nitriles are separated by vacuum distillation and recrystallization.

The 2-phenylglutaronitrile (J) is then converted to the compound represented by Formula (M) which in turn is converted to the diamine of Formula (N) which then is converted to the desired products of Formulas ($II^3$), ($III^3$) or ($IV^3$). The reaction conditions required to convert the 2-phenylglutaranitrile of Formula (J) to the compounds of this invention are essentially the same as the conditions discussed in the section for the preparation of the 5-substituted 1,4,5,6-tetrahydropyrimidines as discussed before.

An alternative route to the preparation of the 1-phenyl-1,3-propanediamine is set forth in Reaction Sequence 4.

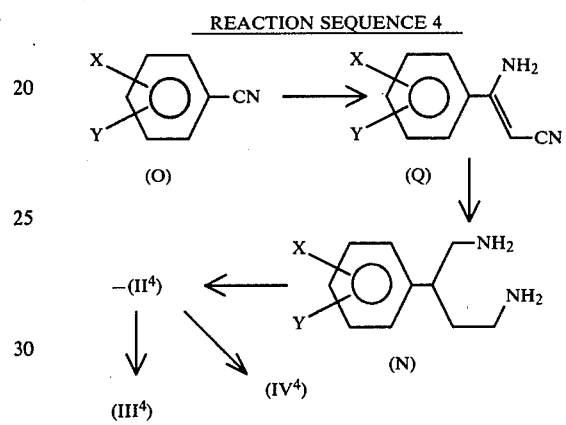

In this sequence, the starting material is the appropriately substituted benzonitrile (O) and the reaction to the β-aminocinnamonitrile (Q) is essentially as that set forth in Chem. Ber., 82, 254 (1949) by Dornow et al, which is incorporated herein by reference. In this Reaction Sequence, the benzonitrile is reacted with acetonitrile to give the β-aminocinnamonitrile represented by Formula (O) which in turn is reduced to give the 1-phenyl-1,3-propanediamine, which is then converted to a compound of Formula ($II^4$), ($III^4$), or ($IV^4$) as discussed hereinbefore.

The respective optical isomers of formulas $II^2-II^4$, $III^2-III^4$, and $IV^2-IV^4$ can be conveniently prepared by using the corresponding optically active isomer starting material of Formulas ($D^2$), (K), (N), etc. The optically active isomer starting material can be obtained by resolution of the corresponding dl mixture by applying conventional resolution procedures. Note for example the procedure described in Ann. Chem., Vol. 494, page 143 (1932). Also see "Tables of Resolving Agents and Optical Resolutions," Samuel H. Wilen, U. of Notre Dame Press (1972), pp. 159–181 and "Stereochemistry of Carbon Compounds" by E. Eliel, McGraw-Hill, 1962, Chap. 4.

The pharmaceutically acceptable salts of the compounds of the invention (including Formulas $II^2-II^4$, $III^2-III^4$, and $IV^1-IV^4$ racemic mixtures and separate optical isomers) can be conveniently prepared by treating the corresponding free base of Formula (I), of the invention, with an acid or via other conventional procedures such as, for example, ion exchange. The free base of Formula (I) may be obtained from the pharmaceutically acceptable salt by treating said salt with a conventional organic or inorganic base such as one employed to liberate a free base from the corresponding acid salt as described hereinbefore.

A further understanding of the invention can be had from the following non-limiting preparations and examples, wherein, unless stated to the contrary, racemates are used as starting materials and corresponding racemic mixtures are obtained as products.

PREPARATION A: 3-phenylglutaronitriles (Reaction Sequence 1)

1. 3-(2,6-dichlorophenyl)glutaronitrile

A solution consisting of 31.5 grams (g) of 2,6-dichlorobenzaldehyde, 39 g of cyanoacetic acid and 2.5 milliliters (ml) of piperidine in 100 ml of pyridine is heated on a steambath for 7 hours. The initial rapid evolution of carbon dioxide gradually diminishes over the reaction time. Most of the solvent is removed under reduced pressure and the residue is dissolved in about 400 ml of benzene. The solution is washed three times with water, three times with dilute sodium bisulfite, again with water, and finally with saturated sodium bicarbonate. The solvent is removed under vacuum and the residue is recrystallized once from 50 ml of methanol and once more from 50 ml of isopropanol to give 12.3 g of 3-(2,6-dichlorophenyl)glutaronitrile having a melting point (mp) of 104°–6° C.

2. Similarly, by following in principle the procedure of Part 1 of this Preparation but substituting an appropriate benzaldehyde for 2,6-dichlorobenzaldehyde, other 3-phenylglutaronitriles are prepared such as 3-phenylglutaronitrile, boiling point (bp) 128°–134° C. at 0.02 mm;
3-(2-chlorophenyl)glutaronitrile, bp about 150° C. at 0.02 mm;
3-(3-chlorophenyl)glutaronitrile;
3-(4-chlorophenyl)glutaronitrile;
3-(2-fluorophenyl)glutaronitrile;
3-(3-fluorophenyl)glutaronitrile;
3-(4-fluorophenyl)glutaronitrile, bp 130°–140° at 0.005 mm;
3-(2-bromophenyl)glutaronitrile;
3-(3-bromophenyl)glutaronitrile, mp 94°–96° C.;
3-(4-bromophenyl)glutaronitrile;
3-(2-iodophenyl)glutaronitrile;
3-(3-iodophenyl)glutaronitrile;
3-(4-iodophenyl)glutaronitrile;
3-(2,3-dichlorophenyl)glutaronitrile;
3-(2,4-dichlorophenyl)glutaronitrile, mp 76°–78° C.;
3-(3,4-dichlorophenyl)glutaronitrile;
3-(3,5-dichlorophenyl)glutaronitrile;
3-(2,5-dichlorophenyl)glutaronitrile;
3-(2,3-didifluorophenyl)glutaronitrile;
3-(2,4-difluorophenyl)glutaronitrile;
3-(3,4-difluorophenyl)glutaronitrile;
3-(2,5-difluorophenyl)glutaronitrile;
3-(2,6-difluorophenyl)glutaronitrile;
3-(3,5-difluorophenyl)glutaronitrile;
3-(2,6-dibromophenyl)glutaronitrile;
3-(2,4-dibromophenyl)glutaronitrile;
3-(3,5-dibromophenyl)glutaronitrile;
3-(2,4-diiodophenyl)glutaronitrile;
3-(2,6-diiodophenyl)glutaronitrile; and the like.

3. 3-(3-methoxyphenyl)glutaronitrile

A solution consisting of 25 g of m-anisaldehyde, 47 g of cyanoacetic acid and 3 ml of piperidine in 120 ml of pyridine is placed in a suitable reaction vessel and kept in a 110° oil-bath for 22 hours. Most of the solvent is removed under reduced pressure and the remaining oil is dissolved in about 400 ml of toluene. The solution is washed sequentially with equal volumes of water, 10% hydrochloric acid and saturated sodium bicarbonate. The washed solution is then concentrated under vacuum and the residue is distilled to give 20.7 g of 3-(3-methoxyphenyl)glutaronitrile, bp 146°–153° at 0.01 mm.

4. Similarly, by following in principle the procedure of Part 3 of this preparation but substituting other substituted benzaldehydes for m-anisaldehyde, other 3-(substituted phenyl)glutaronitriles can be prepared, such as 3-(2-methoxyphenyl)glutaronitrile;
3-(4-methoxyphenyl)glutaronitrile;
3-(2-ethoxyphenyl)glutaronitrile;
3-(3-ethoxyphenyl)glutaronitrile;
3-(4-ethoxyphenyl)glutaronitrile;
3-(2-propoxyphenyl)glutaronitrile;
3-(3-propoxyphenyl)glutaronitrile;
4-(4-propoxyphenyl)glutaronitrile;
3-(4-butoxyphenyl)glutaronitrile;
3-(2-benzyloxyphenyl)glutaronitrile;
3-(3-benzyloxyphenyl)glutaronitrile;
3-(4-benzyloxyphenyl)glutaronitrile, m.p. 140°–143°;
3-(2-methylphenyl)glutaronitrile;
3-(3-methylphenyl)glutaronitrile;
3-(4-methylphenyl)glutaronitrile, bp 124°–130° C./0.02 mm,
3-(2-ethylphenyl)glutaronitrile;
3-(3-ethylphenyl)glutaronitrile;
3-(4-ethylphenyl)glutaronitrile;
3-(2-isopropylphenyl)glutaronitrile;
3-(3-isopropylphenyl)glutaronitrile;
3-(4-isopropylphenyl)glutaronitrile, bp about 180° C./0.05 mm;
3-(2-trifluoromethylphenyl)glutaronitrile
3-(3-trifluoromethylphenyl)glutaronitrile;
3-(4-trifluoromethylphenyl)glutaronitrile;
3-(2-methylthiophenyl)glutaronitrile;
3-(4-methylthiophenyl)glutaronitrile;
3-(2-ethylthiophenyl)glutaronitrile;
3-(4-ethylthiophenyl)glutaronitrile;
3-(2-butylthiophenyl)glutaronitrile;
3-(3-butylthiophenyl)glutaronitrile;
3-(4-methylsulfinylphenyl)glutaronitrile;
3-(4-ethylsulfonylphenyl)glutaronitrile;
3-(2,4-dimethoxyphenyl)glutaronitrile;
3-(2,6-diethoxyphenyl)glutaronitrile;
3-(3,4-dibenzoyloxyphenyl)glutaronitrile;
3-(3,5-diethylthiophenyl)glutaronitrile;
3-(2,6-dimethylsulfinylphenyl)glutaronitrile;
3-(2,6-dimethylsulfonylphenyl)glutaronitrile; and the like.

PREPARATION B: 3-Phenylglutaramides (Reaction Sequence 1)

1. 3-(2,6-dichlorophenyl)glutaramide

Twelve and three-tenths (12.3) of 3-(2,6-dichlorophenyl)glutaronitrile, prepared according to Preparation A, Part 1, is dissolved in a mixture of 70 ml of concentrated sulfuric acid and 3 ml of water. This solution is allowed to stand for 2 days at room temperature and then poured over crushed ice and is neutralized with ammonium hydroxide. The solid precipitate is collected, washed with water and dried under vacuum to give 13.8 g of 3-(2,6-dichlorophenyl)glutaramide, mp 221°–225°.

2. Similarly, by following the procedure of Part 1 of this preparation but substituting other suitable 3-phenylglutaronitriles (such as those set forth in Preparation A, Parts 2 or 5), for 3-(2,6-dichlorophenyl)glutaronitrile, other corresponding 3-phenylglutaramides are obtained such as
3-phenylglutaroamide, melting point 183°–184° C.;
3-(2-chlorophenyl)glutaramide, mp 189° C.;
3-(3-chlorophenyl)glutaramide;
3-(4-chlorophenyl)glutaramide;
3-(2-fluorophenyl)glutaramide;
3-(3-fluorophenyl)glutaramide;
3-(4-fluorophenyl)glutaramide, mp 194°–196° C.;
3-(2-bromophenyl)glutaramide;
3-(3-bromophenyl)glutaramide, mp 168°–170° C.;
3-(4-bromophenyl)glutaramide;
3-(2-iodophenyl)glutaramide;
3-(3-iodophenyl)glutaramide;
3-(4-iodophenyl)glutaramide;
3-(2,3-dichlorophenyl)glutaramide;
3-(2,4-dichlorophenyl)glutaramide, mp 194°–196° C.;
3-(3,4-dichlorophenyl)glutaramide;
3-(3,5-dichlorophenyl)glutaramide;
3-(2,5-dichlorophenyl)glutaramide;
3-(2,3-difluorophenyl)glutaramide;
3(2,4-difluorophenyl)glutaramide;
3-(3,4-difluorophenyl)glutaramide;
3-(2,5-difluorophenyl)glutaramide;
3-(2,6-difluorophenyl)glutaramide;
3-(3,5-difluorophenyl)glutaramide;
3(2,6-dibromophenyl)glutaramide;
3-(2,4-dibromophenyl)glutaramide;
3-(3,5-dibromophenyl)glutaramide;
3-(2,4-diiodophenyl)glutaramide;
3-(2,6-diiodophenyl)glutaramide; and the like.

3. 3-(3-methoxyphenyl)glutaramide

A sample of 18.7 g of 3-(3-methoxyphenyl)glutaronitrile prepared according to Preparation A, Part 3, is dissolved in 250 ml of acetone. This solution is stirred in an ice-bath and added are 125 ml of water, 40 ml of 30% hydrogen peroxide and 25 ml of 10% sodium carbonate. The mixture is allowed to stand at room temperature over night and is then concentrated to a volume of about 125 ml. The residue is cooled and the resulting crystalline precipitate is collected, washed with water and dried under vacuum to give 17.4 g of 3-(3-methoxyphenyl)glutaramide, mp 161°–162°.

4. Similarly, by following in principle the procedure of Part 3 of this preparation, but substituting other suitable 3-phenylglutaramides prepared according to the process of Preparation A, Part 4, other corresponding 3-(substituted phenyl)glutaramides are prepared such as
3-(2-methoxyphenyl)glutaramide;
3-(4-methoxyphenyl)glutaramide;
3-(2-ethoxyphenyl)glutaramide;
3-(3-ethoxyphenyl)glutaramide;
3-(4-ethoxyphenyl)glutaramide;
3-(2-propoxyphenyl)glutaramide;
3-(3-propoxyphenyl)glutaramide;
3-(4-propoxyphenyl)glutaramide;
3-(4-butoxyphenyl)glutaramide;
3-(2-benzoyloxyphenyl)glutaramide;
3-(3-benzyloxyphenyl)glutaramide;
3-(4-benzyloxyphenyl)glutaramide, m.p. 205°–207° C.;
3-(4-methylphenyl)glutaramide, bp 194°–196° C.;
3-(2-methylphenyl)glutaramide;
3-(3-methylphenyl)glutaramide;
3-(3-ethylphenyl)glutaramide;
3-(4-ethylphenyl)glutaramide;
3-(2-ethylphenyl)glutaramide;
3-(2-isopropylphenyl)glutaramide;
3-(3-isopropylphenyl)glutaronitrole;
3-(4-isopropylphenyl)glutaramide, bp 192°–193° C.;
3-(2-trifluoromethylphenyl)glutaramide;
3-(3-trifluoromethylphenyl)glutaramide;
3-(4-trifluoromethylphenyl)glutaramide;
3-(2-methylthiophenyl)glutaramide;
3-(4-methylthiophenyl)glutaramide;
3-(2-ethylthiophenyl)glutaramide;
3-(4-ethylthiophenyl)glutaramide;
3-(2-butylthiophenyl)glutaramide;
3-(3-butylthiophenyl)glutaramide;
3-(4-methsulfinylphenyl)glutaramide;
3-(4-ethylsulfonylphenyl)glutaramide;
3-(2,4-dimethoxyphenyl)glutaramide;
3-(2,6-diethoxyphenyl)glutaramide;
3-(3,4-dibenzyloxyphenyl)glutaramide;
3-(3,5-diethylthiophenyl)glutaramide;
3-(2,6-dimethylsulfinylphenyl)glutaramide;
3-(2,6-dimethylsulfonylphenyl)glutaramide; and the like.

PREPARATION C: 2-Phenyl-1,3-propanediamine
(Reaction Sequence 1)

1. 2-(3-methoxyphenyl)-1,3-propanediamine

A sodium hypobromite solution is prepared from 27 g of sodium hydroxide and 23 g of bromine in 200 ml of water at −3°. 15.2 G of 3-(3-methoxyphenyl)glutaramide (prepared according to Preparation B, Part 1) are added in five equal portions to the sodium hypobromite solution. The mixture is stirred at 0° C. until there is a clear solution and is then stirred at room temperature for 1 hour and finally at 70° for 30 minutes. It is cooled and extracted with twelve 70 ml portions of methylene chloride and with two 70 ml portions of toluene. The combined extracts are dried over sodium sulfate, concentrated and distilled to yield 5.1 g of 2-(3-methoxyphenyl)-1,3-propanediamine, bp 140° C. at 1 mm.

A small amount of the dihydrochloride salt is prepared by dissolving a few drops of the diamine in ethanol hydrogen chloride and adding ether to the resulting solution to crystallize the dihydrochloride of 2-(3-methoxyphenyl)-1,3-propanediamine, mp 232°–234°.

2. Similarly, by following in principle the procedure of Part 1 of this preparation but substituting other suitable 2-phenylglutaramides prepared according to Preparation B, Parts 2, 3, or 4 for 3-(3methoxyphenyl)glutaramide, other 2-phenyl-1,3-propanediamines are prepared, such as
2-phenyl-1,3-propanediamine, bp 85°–87° C./2 mm (as dihydrochloride [diHCl] salt, mp 258°–262° C.);
2-(2-chlorophenyl)1,3-propanediamine, bp 87°–92° C./0.05 mm (di HCl salt, mp 253°–257° C.);
2-(3-chlorophenyl)-1,3-propanediamine;
2-(4-chlorophenyl)-1,3-propanediamine;
2-(2-fluorophenyl)-1,3-propanediamine;
2-(3-fluorophenyl)-1,3-propanediamine;
2-(4-fluorophenyl)-1,3-propanediamine, (diHCl salt mp 292.5°–295° C.);
2-(2-bromophenyl)-1,3-propanediamine;
2-(3-bromophenyl)-1,3-propanediamine, bp 120°–125° C./0.02 mm (diHCl salt, mp 260°–265° C.);
2-(4-bromophenyl)-1,3-propanediamine;
2-(2-iodophenyl)-1,3-propanediamine;
2-(3-iodophenyl)-1,3-propanediamine;
2-(4-iodophenyl)-1,3-propanediamine;
2-(2,3-dichlorophenyl)-1,3-propanediamine;

2-(2,4-dichlorophenyl)-1,3-propanediamine, bp 110° C./0.01 mm (diHCl salt, mp 268°-270° C.);
2-(3,4-dichlorophenyl)-1,3-propanediamine;
2-(3,5-dichlorophenyl)-1,3-propanediamine;
2-(2,5-dichlorophenyl)-1,3-propanediamine;
2-(2,6-dichlorophenyl)-1,3-propanediamine, bp 126°-128° C./0.5 mm (dipicrate salt, mp 253°-255° C.);
2-(2,3-difluorophenyl)-1,3-propanediamine;
2-(2,4-difluorophenyl)-1,3-propanediamine;
2-(3,4-difluorophenyl)-1,3-propanediamine;
2-(2,5-difluorophenyl)-1,3-propanediamine;
2-(2,6-difluorophenyl)-1,3-propanediamine;
2-(3,5-difluorophenyl)-1,3-propanediamine;
2-(3,6-dibromophenyl)-1,3-propanediamine;
2-(2,4-dibromophenyl)-1,3-propanediamine;
2-(3,5-dibromophenyl)-1,3-propanediamine;
2-(2,4-diiodophenyl)-1,3-propanediamine;
2-(2,6-diiodophenyl)-1,3-propanediamine;
2-(2-methoxyphenyl)-1,3-propanediamine;
2-(3-methoxyphenyl)-1,3-propanediamine;
2-(4-methoxyphenyl)-1,3-propanediamine;
2-(2-ethoxyphenyl)-1,3-propanediamine;
2-(3-ethoxyphenyl)-1,3-propanediamine;
2-(4-ethoxyphenyl)-1,3-propanediamine;
2-(2-propoxyphenyl)-1,3-propanediamine;
2-(3-propoxyphenyl)-1,3-propanediamine;
2-(4-propoxyphenyl)-1,3-propanediamine;
2-(4-butoxyphenyl)-1,3-propanediamine;
2-(2-benzyloxyphenyl)-1,3-propanediamine;
2-(3-benzyloxyphenyl)-1,3-propanediamine;
2-(4-benzyloxyphenyl)-1,3-propanediamine;
2-(2-methylphenyl)-1,3-propanediamine;
2-(3-methylphenyl)-1,3-propanediamine;
2-(4-methylphenyl)-1,3-propanediamine;
2-(2-ethylphenyl)-1,3-propanediamine;
2-(3-ethylphenyl)-1,3-propanediamine;
2-(4-ethylphenyl)-1,3-propanediamine;
2-(2-isopropylphenyl)-1,3-propanediamine;
2-(3-isopropylphenyl)-1,3-propanediamine;
2-(4-isopropylphenyl)-1,3-propanediamine, bp 103°-108° C./0.01 mm (diHCl salt, mp 284°-287° C.);
2-(2-trifluoromethylphenyl)-1,3-propanediamine;
2-(3-trifluoromethylphenyl)-1,3-propanediamine;
2-(4-trifluoromethylphenyl)-1,3-propanediamine;
2-(2-methylthiophenyl)-1,3-propanediamine;
2-(4-methylthiophenyl)-1,3-propanediamine;
2-(2-ethylthiophenyl)-1,3-propanediamine;
2-(4-ethylthiophenyl)-1,3-propanediamine;
2-(2-butylthiophenyl)-1,3-propanediamine;
2-(3-butylthiophenyl)-1,3-propanediamine;
2-(4-methsulfinylphenyl)-1,3-propanediamine;
2-(4-ethylsulfonylphenyl)-1,3-propanediamine;
2-(2,4-dimethoxyphenyl)-1,3-propanediamine;
2-(2,6-diethoxyphenyl)-1,3-propanediamine;
2-(3,4-dibenzyloxyphenyl)-1,3-propanediamine;
2-(3,5-diethylthiophenyl)-1,3-propanediamine;
2-(2,6-dimethylsulfinylphenyl)-1,3-propanediamine;
2-(2,6-dimethylsulfonylphenyl)-1,3-propanediamine;
and the like.

PREPARATION D: N-Methyl-2-phenyl-1,3-propane diamines (Reaction Sequence 2)

1. Four and four-tenths (4.4) g of the ethyleneglycol acetal of atropaldehyde is hydrolysed by reaction with 40 ml of water and 250 mg of oxalic acid in 200 ml of ethanol at 70° for about 1 hour. One and four-tenths (1.4) g of N-methylhydrazine is added and the resulting mixture is allowed to stand for 4 hours at room temperature. The mixture is then concentrated to about 50 ml, aqueous sodium bicarbonate is added and the mixture is extracted with methylenechloride. The extract is concentrated and distilled, to give 2.2 g of 4,5-dihydro-1-methyl-4-phenyl-[1H]-pyrrazole, bp 66°-72°/0.03 mm; ms 160 (M+).

A mixture of 3.8 g of 4,5-dihydro-1-methyl-4-phenyl-[1H]-pyrrazole, 50 ml of glacial acetic acid, 10 ml of 10% hydrochloric acid and 1 g of a catalyst consisting of 5% platinum on charcoal is stirred under a hydrogen atmosphere for about 6 hours until the calculated amount of hydrogen has been consumed. The mixture is filtered and the filtrate is concentrated under vacuum. The residue is treated with isopropanol and toluene and is concentrated again to remove as much of the water as possible. The residue is refluxed with ether for 3 hours until a powdery solid forms which is collected by filtration. Recrystallization from ethanol gives N-methyl-2-phenyl-1,3-propanediamine hydrochloride, mp 264°-267° C.

2. In a similar manner by substituting other ethylene glycol acetals of appropriately phenyl-ring substituted atropaldehydes, other N-methyl-2-substituted phenyl-1,3-propanediamines are prepared such as
N-methyl-2-(2-fluorophenyl)-1,3-propanediamine;
N-methyl-2-(3-fluorophenyl)-1,3-propanediamine;
N-methyl-2-(4-fluorophenyl)-1,3-propanediamine;
N-methyl-2-(2-chlorophenyl)-1,3-propanediamine;
N-methyl-2-(3-chlorophenyl)-1,3-propanediamine;
N-methyl-2-(4-chlorophenyl)-1,3-propanediamine;
N-methyl-2-(2-bromophenyl)-1,3-propanediamine;
N-methyl-2-(3-bromophenyl)-1,3-propanediamine;
N-methyl-2-(4-bromophenyl)-1,3-propanediamine;
N-methyl-2-(2-iodophenyl)-1,3-propanediamine;
N-methyl-2-(3-iodophenyl)-1,3-propanediamine;
N-methyl-2-(4-iodophenyl)-1,3-propanediamine;
N-methyl-2-(2,4-dichlorophenyl)-1,3-propanediamine;
N-methyl-2-(3,4-dichlorophenyl)-1,3-propanediamine;
N-methyl-2-(3,5-dichlorophenyl)-1,3-propanediamine;
N-methyl-2-(2,5-dichlorophenyl)-1,3-propanediamine;
N-methyl-2-(2,6-dichlorophenyl)-1,3-propanediamine;
N-methyl-2-(2,3-difluorophenyl)-1,3-propanediamine;
N-methyl-2-(2,4-difluorophenyl)-1,3-propanediamine;
N-methyl-2-(3,4-difluorophenyl)-1,3-propanediamine;
N-methyl-2-(2,5-difluorophenyl)-1,3-propanediamine;
N-methyl-2-(2,6-difluorophenyl)-1,3-propanediamine;
N-methyl-2-(3,5-difluorophenyl)-1,3-propanediamine;
N-methyl-2-(3,6-dibromophenyl)-1,3-propanediamine;
N-methyl-2-(2,4-dibromophenyl)-1,3-propanediamine;
N-methyl-2-(3,5-dibromophenyl)-1,3-propanediamine;
N-methyl-2-(2,4-diiodophenyl)-1,3-propanediamine;
N-methyl-2-(2,6-diiodophenyl)-1,3-propanediamine;
N-methyl-2-(2-hydroxyphenyl)-1,3-propanediamine;
N-methyl-2-(2-methoxyphenyl)-1,3-propanediamine;
N-methyl-2-(3-methoxyphenyl)-1,3-propanediamine;
N-methyl-2-(4-methoxyphenyl)-1,3-propanediamine;
N-methyl-2-(2-ethoxyphenyl)-1,3-propanediamine;
N-methyl-2-(3-ethoxyphenyl)-1,3-propanediamine;
N-methyl-2-(4-ethoxyphenyl)-1,3-propanediamine;
N-methyl-2-(2-propoxyphenyl)-1,3-propanediamine;
N-methyl-2-(3-propoxyphenyl)-1,3-propanediamine;
N-methyl-2-(4-propoxyphenyl)-1,3-propanediamine;
N-methyl-2-(3-isopropoxyphenyl)-1,3-propanediamine;
N-methyl-2-(4-butoxyphenyl)-1,3-propanediamine;
N-methyl-2-(2-benzyloxyphenyl)-1,3-propanediamine;
N-methyl-2-(3-benzyloxyphenyl)-1,3-propanediamine;
N-methyl-2-(4-benzyloxyphenyl)-1,3-propanediamine;

N-methyl-2-(2-methylphenyl)-1,3-propanediamine;
N-methyl-2-(3-methylphenyl)-1,3-propanediamine;
N-methyl-2-(4-methylphenyl)-1,3-propanediamine;
N-methyl-2-(2ethylphenyl)-1,3-propanediamine;
N-methyl-2-(3-ethylphenyl)-1,3-propanediamine;
N-methyl-2-(4-ethylphenyl)-1,3-propanediamine;
N-methyl-2-(3-propylphenyl)-1,3-propanediamine;
N-methyl-2-(2-isopropylphenyl)-1,3-propanediamine;
N-methyl-2-(3-isopropylphenyl)-1,3-propanediamine;
N-methyl-2-(4-isopropylphenyl)-1,3-propanediamine;
N-methyl-2-(4-butylphenyl)-1,3-propanediamine;
N-methyl-2-(2-trifluoromethylphenyl)-1,3-propanediamine;
N-methyl-2-(3-trifluoromethylphenyl)-1,3-propanediamine;
N-methyl-2-(4-trifluoromethylphenyl)-1,3-propanediamine;
N-methyl-2-(2-methylthiophenyl)-1,3-propanediamine;
N-methyl-2-(4-methylthiophenyl)-1,3-propanediamine;
N-methyl-2-(2-ethylthiophenyl)-1,3-propanediamine;
N-methyl-2-(4-ethylthiophenyl)-1,3-propanediamine;
N-methyl-2-(2-butylthiophenyl)-1,3-propanediamine;
N-methyl-2-(3-butylthiophenyl)-1,3-propanediamine;
N-methyl-2-(4-methylsulfinylphenyl)-1,3-propanediamine;
N-methyl-2-(4-ethylsulfonylphenyl)-1,3-propanediamine;
N-methyl-2-(2,4-dimethoxyphenyl)-1,3-propanediamine;
N-methyl-2-(2,6-diethoxyphenyl)-1,3-propanediamine;
N-methyl-2-(3,4-dibenzyloxyphenyl)-1,3-propanediamine;
N-methyl-2-(3,5-diethylthiophenyl)-1,3-propanediamine;
N-methyl-2-(2,6-dimethylsulfinylphenyl)-1,3-propanediamine;
N-methyl-2-(2,6-dimethylsulfonylphenyl)-1,3-propanediamine; and the like.

3. By following in principle the procedure of Parts A and B of this Preparation but substituting other N-alkylhydrazines such as N-ethylhydrazine, N-propylhydrazine or N-butylhydrazine for N-methylhydrazine, other diamines are obtained such as
N-ethyl-2-phenyl-1,3-propanediamine;
N-propyl-2-phenyl-1,3-propanediamine;
N-butyl-2-phenyl-1,3-propanediamine; and the like.

PREPARATION E: 2-Phenylglutaramides (Reaction Sequence 3)

1. Twenty-five g of 4-fluorobenzylcyanide is mixed with approximately 3.5 ml of freshly distilled acrylonitrile in a suitable reaction vessel. To this stirred mixture is added dropwise a solution of 80 mg of sodium methoxide in 1 ml of methanol. When about half of the sodium methoxide is added, there is an exothermic reaction. After all the sodium methoxide is added, the mixture is kept on a steam-bath for 2 hours and is then dissolved in toluene and washed with water. The toluene is removed by evaporation and the residue is separated into its components by fractional distillation to give 18 g of 4-fluorobenzylcyanide, and 2 g of 2-(4-fluorophenyl)glutaronitrile, bp 118°–122° C. at 0.03 mm.

A reaction mixture consisting of 3.5 g of 2-(4-fluorophenyl/glutaronitrile, 25 ml of concentrated sulfuric acid and 1 ml of water is allowed to stand at room temperature over night. The solution is poured into 300 g of ice and is then neutralized with ammonium hydroxide. The product is extracted out with chloroform in a continuous extractor. After three days the product that has formed as a crystalline material in the chloroform is collected to yield 3.01 g of 2-(4-fluorophenyl)glutaramide, m.p. 154°–157° C.

2. Similarly, by following in principle the procedure of Part 3 of this preparation, but substituing other benzylcyanides for 4-fluorobenzylcyanide, other 2-phenylglutaramides are prepared, such as
2-phenylglutaroamide;
2-(2-chlorophenyl)glutaramide;
2-(3-chlorophenyl)glutaramide;
2-(4-chlorophenyl)glutaramide;
2-(2-fluorophenyl)glutaramide;
2-(3-fluorophenyl)glutaramide;
2-(2-bromophenyl)glutaramide;
2-(3-bromophenyl)glutaramide;
2-(4-bromophenyl)glutaramide;
2-(2-iodophenyl)glutaramide;
2-(3-iodophenyl)glutaramide;
2-(4-iodophenyl)glutaramide;
2-(2,3-dichlorophenyl)glutaramide;
2-(2,4-dichlorophenyl)glutaramide;
2-(3,4-dichlorophenyl)glutaramide;
2-(3,5-dichlorophenyl)glutaramide;
2-(2,5-dichlorophenyl)glutaramide;
2-(2,3-difluorophenyl)glutaramide;
2-(2,4-difluorophenyl)glutaramide;
2-(3,4-difluorophenyl)glutaramide;
2-(2,5-difluorophenyl)glutaramide;
2-(2,6-difluorophenyl)glutaramide;
2-(3,5-difluorophenyl)glutaramide;
2-(2,6-dibromophenyl)glutaramide;
2-(2,4-dibromophenyl)glutaramide;
2-(3,5-dibromophenyl)glutaramide;
2-(2,4-diiodophenyl)glutaramide;
2-(2,6-diiodophenyl)glutaramide;
2-(3-methoxyphenyl)glutaramide;
2-(2-methoxyphenyl)glutaramide;
2-(4-methoxyphenyl)glutaramide;
2-(2-ethoxyphenyl)glutaramide;
2-(3-ethoxyphenyl)glutaramide;
2-(4-ethoxyphenyl)glutaramide;
2-(2-propoxyphenyl)glutaramide;
2-(3-propoxyphenyl)glutaramide;
2-(4-propoxyphenyl)glutaramide;
2-(4-butoxyphenyl)glutaramide;
2-(2-benzyloxyphenyl)glutaramide;
2-(3-benzyloxyphenyl)glutaramide;
2-(4-benzyloxyphenyl)glutaramide;
2-(2-methylphenyl)glutaramide;
2-(3-methylphenyl)glutaramide;
2-(4-methylphenyl)glutaramide;
2-(2-ethylphenyl)glutaramide;
2-(3-ethylphenyl)glutaramide;
2-(4-ethylphenyl)glutaramide;
2-(2-isopropylphenyl)glutaramide;
2-(3-isopropylphenyl)glutaronitrole;
2-(4-isopropylphenyl)glutaramide;
2-(2-trifluoromethylphenyl)glutaramide;
2-(3-trifluoromethylphenyl)glutaramide;
2-(4-trifluoromethylphenyl)glutaramide;
2-(2-methylthiophenyl)glutaramide;
2-(4-methylthiophenyl)glutaramide;
2-(2-ethylthiophenyl)glutaramide;
2-(4-ethylthiophenyl)glutaramide;
2-(2-butylthiophenyl)glutaramide;
2-(3-butylthiophenyl)glutaramide;

2-(4-methylsulfinylphenyl)glutaramide;
2-(4-ethylsulfonylphenyl)glutaramide;
2-(2,4-dimethoxyphenyl)glutaramide;
2-(2,6-diethoxyphenyl)glutaramide;
2-(3,5-diethylthiophenyl)glutaramide;
2-(2,6-dimethylsulfinylphenyl)glutaramide;
2-(2,6-dimethylsulfonylphenyl)glutaramide; and the like.

PREPARATION F: 1-phenyl-1,3-propanediamines
(Reaction Sequence 3)

A. 1-Phenyl-1,3-propanediamine

A solution of 27 g of potassium hydroxide in 150 ml of water is cooled to −2° C. and 17 g of bromine is added in a thin stream. The mixture is stirred for 10 min. and 10 g of 2-phenylglutaramide is then added. Stirring is continued while the temperature is kept at −3° to +2° C. until there is a clear solution (about 15 min.). The solution is then stirred at room temperature for 30 mins. and finally at 60° C. for 90 min. It is cooled and extracted several times with methylene chloride and the combined extracts are dried over sodium sulfate, filtered and concentrated. The residue is distilled to yield 4.2 g of 1-phenyl-1,3-propanediamine, b.p. 84°–87° C. at 0.5 mm.

When 2.2 g of the diamine is dissolved in 25 ml of ethanol that contains 1.3 g of hydrogen chloride there is crystallization of the dihydrochloride salt which is collected and dried at 80° C. under vacuum to yield 2.8 g of 1-phenyl-1,3-propanediamine dihydrochloride, m.p. 244°–246° C.

B. Other 1-phenylpropanediames are prepared by following in principle the procedure of Part A of this procedure substituting other 2-phenylglutaramides of Part 2 of Preparation E for 2-phenylgutaramide in Part A of this procedure.

PREPARATION G: β-Amino-2-cinnamonitriles
(Reaction Sequence 4)

1. β-Amino-2-trifluoromethylcinnamonitrile

A mixture consisting of 9.3 g of 2-trifluoromethylbenzonitrile, 4.5 g of acetonitrile, 4.3 g of sodium amide and 100 ml of ether is stirred and refluxed under nitrogen over night. The resulting solid is collected on a Buchner-funnel, washed with ether and dissolved in approximately 100 ml of cold ethanol. Crushed ice is added to this solution until the total volume is about 700 ml. This mixture is allowed to stand for several hours. The resulting solid precipitate is collected by filtration then dissolved in methanol and decolorizing charcoal is added. The charcoal/methanol mixture is filtered and the filtrate is gradually treated with water until crystallization is judged complete. The crystalline solid is collected and dried under vacuum, to give 7.75 g of β-amino-2-trifluoromethylcinnamonitrile, mp 101°–103°.

2. Similarly, by following in principle the procedure of Part 1 of this Preparation, but substituting other appropriately substituted benzonitriles for 2-trifluoromethylbenzonitrile, other corresponding β-amino-substituted cinnamonitriles are prepared such as
β-aminocinnamonitrile;
β-amino-2-fluorocinnamonitrile;
β-amino-3-fluorocinnamonitrile;
β-amino-4-fluorocinnamonitrile;
β-amino-2-chlorocinnamonitrile;
β-amino-3-chlorocinnamonitrile;
β-amino-4-chlorocinnamonitrile;
β-amino-3-bromocinnamonitrile;
β-amino-4-iodocinnamonitrile;
β-amino-2-methylcinnamonitrile;
β-amino-4-methylcinnamonitrile, mp 111°–113° C.;
β-amino-2-ethylcinnamonitrile;
β-amino-4-t-butylcinnamonitrile;
β-amino-2-methoxycinnamonitrile, mp 74°–75° C.;
β-amino-3-ethoxycinnamonitrile;
β-amino-4-isopropoxycinnamonitrile;
β-amino-2-methylthiocinnamonitrile;
β-amino-4-isobutylthiocinnamonitrile;
β-amino-4-methylsulfinylcinnamonitrile;
β-amino-4-methylsulfonylcinnamonitrile;
β-amino-2,4-difluorocinnamonitrile;
β-amino-2,6-dichlorocinnamonitrile;
β-amino-2,6-dibromocinnamonitrile;
β-amino-2,4-diiodocinnamonitrile;
β-amino-2,4-dimethylcinnamonitrile;
β-amino-2,6-disopropylcinnamonitrile;
β-amino-2,4-dimethoxycinnamonitrile;
β-amino-2,6-diethoxycinnamonitrile;
β-amino-2,4-dimethylthiocinnamonitrile;
β-amino-2,6-dimethylsulfinylcinnamonitrile; and the like.

PREPARATION H: 1-phenyl-1,3-propanediamines
(Reaction Sequence 4)

1. 1-(2-Trifluoromethylphenyl)-1,3-propanediamine

Sixty (60) ml of 1 molar borane in tetrahydrofuran is added to a solution of 7.6 g of β-amino-2-trifluoromethylcinnamonitrile (prepared according to Preparation D, Part 1) in 100 ml of ether. The mixture is stirred at room temperature overnight, then treated with 10 ml of water, and stirred for 45 minutes. The resulting mixture is concentrated under reduced pressure and 200 ml of isopropanol and 80 ml of 20% hydrochloric acid are added thereto. This mixture is refluxed for 2 hours, then concentrated to a small volume. The residue is made alkaline by addition of excess of 20% sodium hydroxide and is extracted 3 times with methylene chloride. The extracts are combined, concentrated and distilled to give 1.7 g of 1-(2-trifluoromethylphenyl)-1,3-propanediamine, bp 73°–77° C./0.1 mm.

The hydrochloric salt is obtained by dissolving the diamine in ethanolic hydrogen chloride and adding ether to this solution to give the diHCl salt of 1-(2-trifluoromethylphenyl)-1,3-propanediamine, mp 213°–127°.

2. Similarly, by following in principle the process of Part 1 of this preparation but substituting a suitable β-aminocinnamonitrile (prepared according to Preparation D, Part 2) for β-amino-2-trifluoromethylcinnamonitrile, other corresponding propanediamines are prepared such as
1-phenyl-1,3-propanediamine, bp 84°–87° C./0.5 mm (diHCl salt, mp 244°–246° C.);
1-(2-fluorophenyl)-1,3-propanediamine;
1-(3-fluorophenyl)-1,3-propanediamine;
1-(4-fluorophenyl)-1,3-propanediamine, bp 84°–88° C./0.7 mm (diHCl salt 262°–266° C.);
1-(2-chlorophenyl)-1,2-propanediamine;
1-(3-chlorophenyl)-1,2-propanediamine;
1-(4-chlorophenyl)-1,2-propanediamine;
1-(3-bromophenyl)-1,2-propanediamine;
1-(4-iodophenyl)-1,2-propanediamine;
1-(2-methylphenyl)-1,2-propanediamine;
1-(4-methylphenyl)-1,2-propanediamine;
1-(2-ethylphenyl)-1,2-propanediamine;
1-(4-t-butylphenyl)-1,2-propanediamine;

1-(2-methoxyphenyl)-1,2-propanediamine;
1-(3-methoxyphenyl)-1,2-propanediamine, b.p. 120°–126° C. at 1 mm (diHCl salt, m.p. 225°–227° C.);
1-(3-ethoxyphenyl)-1,2-propanediamine;
1-(4-isopropoxyphenyl)-1,2-propanediamine;
1-(2-methylthiophenyl)-1,2-propanediamine;
1-(4-isobutylthiophenyl)-1,2-propanediamine;
1-(4-methylsulfinylphenyl)-1,2-propanediamine;
1-(4-methylsulfonylphenyl)-1,2-propanediamine;
1-(2,4-difluorophenyl)-1,2-propanediamine;
1-(2,6-dichlorophenyl)-1,2-propanediamine;
1-(2,6-dibromophenyl)-1,2-propanediamine;
1-(2,4-diiodophenyl)-1,2-propanediamine;
1-(2,4-dimethylphenyl)-1,2-propanediamine;
1-(2,6-disopropylphenyl)-1,2-propanediamine;
1-(2,4-dimethoxyphenyl)-1,2-propanediamine;
1-(2,6-diethoxyphenyl)-1,2-propanediamine;
1-(2,4-dimethylthiophenyl)-1,2-propanediamine;
1-(2,6-dimethylsulfinyl; and the like.

EXAMPLE 1:
2-Amino-5-phenyl-1,4,5,6-tetrahydropyrimidines.

A. A solution of 1.55 g of 2-(3-bromophenyl)-1,3-propanediamine (prepared in accordance with Preparation C, Part 2) and 0.72 g of cyanogenbromide in 300 ml of methanol is maintained at room temperature for three days and is then refluxed for 6 hours. The solvent is evaporated off by a rotary evaporator. The residue is dissolved in boiling isopropanol which then is filtered through a steam-jacketed funnel. The crystals which form as the filtrate are cooled is collected by filtration and dried under vacuum to give 0.87 g of the hydrobromide salt of 2-amino-5-(3-bromophenyl)-1,4,5,6-tetrahydropyrimidine, mp 223°–227° C.

B. A stirred mixture consisting of 3.25 g of 2-phenyl-1,3-propanediamine (prepared in accordance with Preparation C) and 3.02 g of 2-methyl-2-thiopseudourea sulfate ([CH$_3$SC(NH)NH$_2$]$_2$.H$_2$SO$_4$) in a small flask is immersed in a 245° C. oil bath. The temperature is raised to 265° C. when the reaction mixture solidifies. When the reaction mixture melts again, it is stirred for about five minutes then is removed from the oil-bath. The contents are refluxed with 50 ml of methanol until a powder is formed. The mixture is cooled and the solid product is collected on a Buchner-funnel, washed with 30% ether in methanol and is air-dried to give 3.7 g of crude product. Recrystallization from 20 ml of water yields 2.25 g of 2-amino-5-phenyl-1,4,5,6-tetrahydropyrimidine sulfate, mp 264°–267° C.

C. By following in principle the procedures of Parts A or B of this example but substituting other appropriate 2-(substituted phenyl)-1,3-propanediamines prepared according to Preparation C for 2-(3-bromophenyl)-1,3-propanediamine and 2-phenyl-1,3-propanediamine other compounds of this invention are prepared such as
2-amino-5-(2-chlorophenyl)-1,4,5,6-tetrahydropyrimidine;
2-amino-5-(3-chlorophenyl)-1,4,5,6-tetrahydropyrimidine;
2-amino-5-(4-chlorophenyl)-1,4,5,6-tetrahydropyrimidine;
2-amino-5-(2-fluorophenyl)-1,4,5,6-tetrahydropyrimidine;
2-amino-5-(3-fluorophenyl)-1,4,5,6-tetrahydropyrimidine;
2-amino-5-(4-fluorophenyl)-1,4,5,6-tetrahydropyrimidine;
2-amino-5-(2-bromophenyl)-1,4,5,6-tetrahydropyrimidine;
2-amino-5-(4-bromophenyl)-1,4,5,6-tetrahydropyrimidine;
2-amino-5-(2-iodophenyl)-1,4,5,6-tetrahydropyrimidine;
2-amino-5-(3-iodophenyl)-1,4,5,6-tetrahydropyrimidine;
2-amino-5-(4-iodophenyl)-1,4,5,6-tetrahydropyrimidine;
2-amino-5-(2,4-dichlorophenyl)-1,4,5,6-tetrahydropyrimidine;
2-amino-5-(3,5-dichlorophenyl)-1,4,5,6-tetrahydropyrimidine;
2-amino-5-(2,5-dichlorophenyl)-1,4,5,6-tetrahydropyrimidine;
2-amino-5-(2,6-dichlorophenyl)-1,4,5,6-tetrahydropyrimidine;
2-amino-5-(2,3-difluorophenyl)-1,4,5,6-tetrahydropyrimidine;
2-amino-5-(2,4-difluorophenyl)-1,4,5,6-tetrahydropyrimidine;
2-amino-5-(2,5-difluorophenyl)-1,4,5,6-tetrahydropyrimidine;
2-amino-5-(2,6-difluorophenyl)-1,4,5,6-tetrahydropyrimidine;
2-amino-5-(3,5-difluorophenyl)-1,4,5,6-tetrahydropyrimidine;
2-amino-5-(3,6-dibromophenyl)-1,4,5,6-tetrahydropyrimidine;
2-amino-5-(2,4-dibromophenyl)-1,4,5,6-tetrahydropyrimidine;
2-amino-5-(3,5-dibromophenyl)-1,4,5,6-tetrahydropyrimidine;
2-amino-5-(2,4-diiodophenyl)-1,4,5,6-tetrahydropyrimidine;
2-amino-5-(2,6-diiodophenyl)-1,4,5,6-tetrahydropyrimidine;
2-amino-5-(2-trifluoromethylphenyl)-1,4,5,6-tetrahydropyrimidine;
2-amino-5-(2-methoxyphenyl)-1,4,5,6-tetrahydropyrimidine;
2-amino-5-(4-methoxyphenyl)-1,4,5,6-tetrahydropyrimidine;
2-amino-5-(2-ethoxyphenyl)-1,4,5,6-tetrahydropyrimidine;
2-amino-5-(3-ethoxyphenyl)-1,4,5,6-tetrahydropyrimidine;
2-amino-5-(4-ethoxyphenyl)-1,4,5,6-tetrahydropyrimidine;
2-amino-5-(2-propoxyphenyl)-1,4,5,6-tetrahydropyrimidine;
2-amino-5-(3-propoxyphenyl)-1,4,5,6-tetrahydropyrimidine;
2-amino-5-(4-propoxyphenyl)-1,4,5,6-tetrahydropyrimidine;
2-amino-5-(4-butoxyphenyl)-1,4,5,6-tetrahydropyrimidine;
2-amino-5-(4-methylphenyl)-1,4,5,6-tetrahydropyrimidine;
2-amino-5-(2-methylphenyl)-1,4,5,6-tetrahydropyrimidine;
2-amino-5-(3-methylphenyl)-1,4,5,6-tetrahydropyrimidine;
2-amino-5-(3-ethylphenyl)-1,4,5,6-tetrahydropyrimidine;
2-amino-5-(4-ethylphenyl)-1,4,5,6-tetrahydropyrimidine;

2-amino-5-(2-ethylphenyl)-1,4,5,6-tetrahydropyrimidine;
2-amino-5-(2-isopropylphenyl)-1,4,5,6-tetrahydropyrimidine;
2-amino-5-(3-isopropylphenyl)-1,4,5,6-tetrahydropyrimidine;
2-amino-5-(4-isopropylphenyl)-1,4,5,6-tetrahydropyrimidine;
2-amino-5-(2-trifluoromethylphenyl)-1,4,5,6-tetrahydropyrimidine
2-amino-5-(3-trifluoromethylphenyl)-1,4,5,6-tetrahydropyrimidine;
2-amino-5-(4-trifluoromethylphenyl)-1,4,5,6-tetrahydropyrimidine;
2-amino-5-(2-methylthiophenyl)-1,4,5,6-tetrahydropyrimidine;
2-amino-5-(4-methylthiophenyl)-1,4,5,6-tetrahydropyrimidine;
2-amino-5-(2-ethylthiophenyl)-1,4,5,6-tetrahydropyrimidine;
2-amino-5-(4-ethylthiophenyl)-1,4,5,6-tetrahydropyrimidine;
2-amino-5-(2-butylthiophenyl)-1,4,5,6-tetrahydropyrimidine;
2-amino-5-(3-butylthiophenyl)-1,4,5,6-tetrahydropyrimidine;
2-amino-5-(4-methsulfinylphenyl)-1,4,5,6-tetrahydropyrimidine;
2-amino-5-(4-ethylsulfonylphenyl)-1,4,5,6-tetrahydropyrimidine;
2-amino-5-(2,4-dimethoxyphenyl)-1,4,5,6-tetrahydropyrimidine;
2-amino-5-(2,6-diethoxyphenyl)-1,4,5,6-tetrahydropyrimidine;
2-amino-5-(3,5-diethylthiophenyl)-1,4,5,6-tetrahydropyrimidine;
2-amino-5-(2,6-dimethylsulfinylphenyl)-1,4,5,6-tetrahydropyrimidine;
2-amino-5-(2,6-dimethylsulfonylphenyl)-1,4,5,6-tetrahydropyrimidine; and the like.

EXAMPLE 2: 1-Alkyl 2-amino-5-phenyl-1,4,5,6-tetrahydropyrimidines.

A. 1-methyl-2-amino-5-phenyl-1,4,5,6-tetrahydropyrimidine

A slurry of 0.55 g of the dihydrochloride salt of N-methyl-2-phenyl-1,3-propanediamine in 25 ml of ethanol is stirred with 0.3 g of sodium methoxide for 30 min. The precipitated sodium chloride is removed by filtration and the filtrate is concentrated. The residue is mixed with 0.322 g of 2-methyl-2-thiopseudourea sulfate and the mixture is stirred in a 240° C. oil-bath for 10 min. The crude reaction product is then refluxed with isopropanol for 2 hours, cooled and the solid is collected and recrystallized from 6–7 ml of water to give 0.2 g of the sulfate salt of 1-methyl-2-amino-5-phenyl-1,4,5,6-tetrahydropyrimidine, m.p. 254°–257° C.

B. In a similar manner, by following in principle the procedure of Part A of this example but substituting other N-methyl-2-phenyl-1,3-propanediamines prepared in accordance with Preparation D, Part 2 for N-methyl-2-phenyl-1,3-propanediamine other compounds of this invention are prepared such as 1-methyl-5-(2-chlorophenyl)-1,4,5,6-tetrahydropyrimidine;
1-methyl-2-amino-5-(3-chlorophenyl)-1,4,5,6-tetrahydropyrimidine;
1-methyl-5-(4-chlorophenyl)-1,4,5,6-tetrahydropyrimidine;
1-methyl-5-(2-fluorophenyl)-1,4,5,6-tetrahydropyrimidine;
1-methyl-5-(3-fluorophenyl)-1,4,5,6-tetrahydropyrimidine;
1-methyl-5-(4-fluorophenyl)-1,4,5,6-tetrahydropyrimidine;
1-methyl-5-(2-bromophenyl)-1,4,5,6-tetrahydropyrimidine;
1-methyl-5-(4-bromophenyl)-1,4,5,6-tetrahydropyrimidine;
1-methyl-5-(2-iodophenyl)-1,4,5,6-tetrahydropyrimidine;
1-methyl-5-(3-iodophenyl)-1,4,5,6-tetrahydropyrimidine;
1-methyl-5-(4-iodophenyl)-1,4,5,6-tetrahydropyrimidine;
1-methyl-5-(2,4-dichlorophenyl)-1,4,5,6-tetrahydropyrimidine;
1-methyl-5-(3,5-dichlorophenyl)-1,4,5,6-tetrahydropyrimidine;
1-methyl-5-(2,5-dichlorophenyl)-1,4,5,6-tetrahydropyrimidine;
1-methyl-5-(2,6-dichlorophenyl)-1,4,5,6-tetrahydropyrimidine;
1-methyl-5-(2,3-difluorophenyl)-1,4,5,6-tetrahydropyrimidine;
1-methyl-2-amino-5-(2,4-difluorophenyl)-1,4,5,6-tetrahydropyrimidine;
1-methyl-5-(2,5-difluorophenyl)-1,4,5,6-tetrahydropyrimidine;
1-methyl-5-(2,6-difluorophenyl)-1,4,5,6-tetrahydropyrimidine;
1-methyl-5-(3,5-difluorophenyl)-1,4,5,6-tetrahydropyrimidine;
1-methyl-5-(3,6-dibromophenyl)-1,4,5,6-tetrahydropyrimidine;
1-methyl-5-(2,4-dibromophenyl)-1,4,5,6-tetrahydropyrimidine;
1-methyl-5-(3,5-dibromophenyl)-1,4,5,6-tetrahydropyrimidine;
1-methyl-5-(2,4-diiodophenyl)-1,4,5,6-tetrahydropyrimidine;
1-methyl-5-(2,6-diiodophenyl)-1,4,5,6-tetrahydropyrimidine;
1-methyl-5-(2-trifluoromethylphenyl)-1,4,5,6-tetrahydropyrimidine;
1-methyl-5-(2-methoxyphenyl)-1,4,5,6-tetrahydropyrimidine;
1-methyl-5-(4-methoxyphenyl)-1,4,5,6-tetrahydropyrimidine;
1-methyl-5-(2-ethoxyphenyl)-1,4,5,6-tetrahydropyrimidine;
1-methyl-5-(3-ethoxyphenyl)-1,4,5,6-tetrahydropyrimidine;
1-methyl-5-(4-ethoxyphenyl)-1,4,5,6-tetrahydropyrimidine;
1-methyl-2-amino-5-(2-propoxyphenyl)-1,4,5,6-tetrahydropyrimidine;
1-methyl-5-(3-propoxyphenyl)-1,4,5,6-tetrahydropyrimidine;
1-methyl-5-(4-propoxyphenyl)-1,4,5,6-tetrahydropyrimidine;
1-methyl-5-(4-butoxyphenyl)-1,4,5,6-tetrahydropyrimidine;
1-methyl-5-(4-methylphenyl)-1,4,5,6-tetrahydropyrimidine;

1-methyl-5-(2-methylphenyl)-1,4,5,6-tetrahydropyrimidine;
1-methyl-5-(3-methylphenyl)-1,4,5,6-tetrahydropyrimidine;
1-methyl-5-(3-ethylphenyl)-1,4,5,6-tetrahydropyrimidine;
1-methyl-5-(4-ethylphenyl)-1,4,5,6-tetrahydropyrimidine;
1-methyl-5-(2-ethylphenyl)-1,4,5,6-tetrahydropyrimidine;
1-methyl-5-(2-isopropylphenyl)-1,4,5,6-tetrahydropyrimidine;
1-methyl-5-(3-isopropylphenyl)-1,4,5,6-tetrahydropyrimidine;
1-methyl-5-(4-isopropylphenyl)-1,4,5,6-tetrahydropyrimidine;
1-methyl-5-(2-trifluoromethylphenyl)-1,4,5,6-tetrahydropyrimidine;
1-methyl-5-(3-trifluoromethylphenyl)-1,4,5,6-tetrahydropyrimidine;
1-methyl-2-amino-5-(4-trifluoromethylphenyl)-1,4,5,6-tetrahydropyrimidine;
1-methyl-5-(2-methylthiophenyl)-1,4,5,6-tetrahydropyrimidine;
1-methyl-5-(4-methylthiophenyl)-1,4,5,6-tetrahydropyrimidine;
1-methyl-5-(2-ethylthiophenyl)-1,4,5,6-tetrahydropyrimidine;
1-methyl-5-(4-ethylthiophenyl)-1,4,5,6-tetrahydropyrimidine;
1-methyl-5-(2-butylthiophenyl)-1,4,5,6-tetrahydropyrimidine;
1-methyl-5-(3-butylthiophenyl)-1,4,5,6-tetrahydropyrimidine;
1-methyl-5-(4-methsulfinylphenyl)-1,4,5,6-tetrahydropyrimidine;
1-methyl-5-(4-ethylsulfonylphenyl)-1,4,5,6-tetrahydropyrimidine;
1-methyl-5-(2,4-dimethoxyphenyl)-1,4,5,6-tetrahydropyrimidine;
1-methyl-5-(2,6-diethoxyphenyl)-1,4,5,6-tetrahydropyrimidine;
1-methyl-5-(3,5-diethylthiophenyl)-1,4,5,6-tetrahydropyrimidine;
1-methyl-5-(2,6-dimethylsulfinylphenyl)-1,4,5,6-tetrahydropyrimidine;
1-methyl-2-amino-5-(2,6-dimethylsulfonylphenyl)-1,4,5,6-tetrahydropyrimidine; and the like.

C. In a similar manner, by following in principle the procedure of Part A of this example but substituting other N-alkyl-2-phenyl-1,3-propanediamines prepared in accordance with Preparation D, Part 3 for N-methyl-2-phenyl-1,3-propanediamine other compounds of this invention are prepared such as
1-ethyl-2-amino-5-phenyl-1,4,5,6-tetrahydropyrimidine;
1-propyl-2-amino-5-phenyl-1,4,5,6-tetrahydropyrimidine;
1-butyl-2-amino-5-phenyl-1,4,5,6-tetrahydropyrimidine;
and other N-alkyl homologs of the compounds of Part B of this Example.

EXAMPLE 3:
2-Alkylcarbonylamino-5-phenyl-1,4,5,6-tetrahydropyrimidines

A. Acetamido-5-phenyl-1,4,5,6-tetrahydropyrimidine
A slurry of 600 mg (2.67 mmole) of the sulfate salt of 2-amino-5-phenyl-1,4,5,6-tetrahydropyrimidine (prepared in accordance with Example 1) in 50 ml of ethanol and 145 mg (2.67 mmole) of sodium methoxide are stirred for 2 hours. The mixture is filtered to remove the insoluble sodium chloride and the solvent is removed under vacuum. The oil residue is dissolved in 100 ml of methylene chloride, 415 mg (1.33 mmole) of N,N',N",N'''-tetraacetylglycoluril is added and the resulting solutions is stirred at room temperature overnight. A precipitate that has formed is removed by filtration and the filtrate is concentrated. The residue is treated with approximately 25 ml of an acetonitrile-ethyl=acetate mixture and the insoluble product is collected by filtration to yield 320 mg of a product having a m.p. 241°–245° C. Upon purification by recrystallization from methanol, 2-acetamido-5-phenyl-1,4,5,6-tetrahydropyrimidine is obtained, m.p. 246°–249° C.

B. Similarly, by following the procedure of Part A of this example but substituting tetrapropionylglycoluril or tetrabutyrylglycoluril for tetracetylglycoluril other amides of this invention are prepared such as
2-propionamido-5-phenyl-1,4,5,6-tetrahydropyrimidine or
2-butyramido-5-phenyl-1,4,5,6-tetrahydropyrimidine.

C. Similarly, by following the procedures of Parts A and B of this example, but substituting the other 2-amino-5-phenyl-1,4,5,6-tetrahydropyrimidine of Example 1, Part C. for 2-amino-5-phenyl-1,4,5,6-tetrahydropyrimide, the corresponding 2-acetamido, 2-propionamido or 2-butyramido-5-phenyl-1,4,5,6-tetrahydropyrimidines are prepared.

EXAMPLE 4: 1-Alkyl 2-alkylcarbonylamino-4-phenyl-1,4,5,6-tetrahydropyrimidines A. By following in principle the procedure of Example 3, Parts A and B but substituting 1-methyl-2-amino-5-phenyl-1,4,5,6-tetrahydropyrimidine for 2-amino-5-phenyl-1,4,5,6-tetrahydropyrimidine other compounds of this invention are prepared such as
1-methyl-2-acetamido-5-phenyl-1,4,5,6-tetrahydropyrimidine;
1-methyl-2-propionamido-5-phenyl-1,4,5,6-tetrahydropyrimidine;
1-methyl-2-butyramido-5-phenyl-1,4,5,6-tetrahydropyrimidine; and the like.

B. Similarly, by following the procedures of Part A of this example, but substituting the other 1-alkyl-2-amino-5-phenyl-1,4,5,6-tetrahydropyrimidine of Example 2, Part C for 1-methyl-2-amino-5-phenyl-1,4,5,6-tetrahydropyrimide, the corresponding 1-alkyl-2-acetamido, 2-propionamido or 2-butyramido-5-phenyl-1,4,5,6-tetrahydropyrimidines are prepared which correspond to the 2-amines of Example 2, Part C.

EXAMPLE 5:
2-Alkoxycarbonylamino-5-phenyl-1,4,5,6-tetrahydropyrimidines

A. 2-Methoxycarbonylamino-5-(3-methoxyphenyl)-1,4,5,6-tetrahydropyrimidine
A solution of 2.61 g (14.5 m. mole) of 2-(3-methoxyphenyl)-1,3-propanediamine in 200 ml of methanol is combined with a solution of 3.0 g (14.55 m. mole) of 1,3-bis(methoxycarbonyl)-S-methylisothiourea in 200 ml of methanol and allowed to stand at room temperature over night. The crystalline product which separates is collected, washed with methanol and dried at 78° under vacuum to give 2.62 g of 2-methoxycarbonylamino-5-(3-methoxyphenyl)-1,4,5,6-tetrahydropyrimidine, mp 218°–221°.

B. Similarly, by following in principle the process of Part A of this example but substituting other 2-(optionally substituted phenyl)-1,3-propanediamines prepared according to the process of Preparation C, Part 2 for 2-(3-methoxyphenyl)-1,3-propanediamine), other compounds of this invention are prepared such as
2-methoxycarbonylamino-5-phenyl-1,4,5,6-tetrahydropyrimidine, m.p. 333°–336° C.;
2-methoxycarbonylamino-5-(2-chlorophenyl)-1,4,5,6-tetrahydropyrimidine, mp 353°–357° C.;
2-methoxycarbonylamino-5-(3-chlorophenyl)-1,4,5,6-tetrahydropyrimidine;
2-methoxycarbonylamino-5-(4-chlorophenyl)-1,4,5,6-tetrahydropyrimidine;
2-methoxycarbonylamino-5-(2-fluorophenyl)-1,4,5,6-tetrahydropyrimidine;
2-methoxycarbonylamino-5-(3-fluorophenyl)-1,4,5,6-tetrahydropyrimidine;
2-methoxycarbonylamino-5-(4-fluorophenyl)-1,4,5,6-tetrahydropyrimidine, mp 225°–235° C. (decomposes) mp HCl salt 179°–182° C.;
2-methoxycarbonylamino-5-(2-bromophenyl)-1,4,5,6-tetrahydropyrimidine;
2-methoxycarbonylamino-5-(3-bromophenyl)-1,4,5,6-tetrahydropyrimidine, mp 213°–215° C.;
2-methoxycarbonylamino-5-(4-bromophenyl)-1,4,5,6-tetrahydropyrimidine;
2-methoxycarbonylamino-5-(2-iodophenyl)-1,4,5,6-tetrahydropyrimidine;
2-methoxycarbonylamino-5-(3-iodophenyl)-1,4,5,6-tetrahydropyrimidine;
2-methoxycarbonylamino-5-(4-iodophenyl)-1,4,5,6-tetrahydropyrimidine;
2-methoxycarbonylamino-5-(2,4-dichlorophenyl)-1,4,5,6-tetrahydropyrimidine, (HCl salt, mp 209°–210° C.);
2-methoxycarbonylamino-5-(3,5-dichlorophenyl)-1,4,5,6-tetrahydropyrimidine;
2-methoxycarbonylamino-5-(2,5-dichlorophenyl)-1,4,5,6-tetrahydropyrimidine;
2-methoxycarbonylamino-5-(2,6-dichlorophenyl)-1,4,5,6-tetrahydropyrimidine, m.p. 231°–234° C.;
2-methoxycarbonylamino-5-(2,3-difluorophenyl)-1,4,5,6-tetrahydropyrimidine;
2-methoxycarbonylamino-5-(2,4-difluorophenyl)-1,4,5,6-tetrahydropyrimidine;
2-methoxycarbonylamino-5-(2,5-difluorophenyl)-1,4,5,6-tetrahydropyrimidine;
2-methoxycarbonylamino-5-(2,6-difluorophenyl)-1,4,5,6-tetrahydropyrimidine;
2-methoxycarbonylamino-5-(3,5-difluorophenyl)-1,4,5,6-tetrahydropyrimidine;
2-methoxycarbonylamino-5-(3,6-dibromophenyl)-1,4,5,6-tetrahydropyrimidine;
2-methoxycarbonylamino-5-(2,4-dibromophenyl)-1,4,5,6-tetrahydropyrimidine;
2-methoxycarbonylamino-5-(3,5-dibromophenyl)-1,4,5,6-tetrahydropyrimidine;
2-methoxycarbonylamino-5-(2,4-diiodophenyl)-1,4,5,6-tetrahydropyrimidine;
2-methoxycarbonylamino-5-(2,6-diiodophenyl)-1,4,5,6-tetrahydropyrimidine;
2-methoxycarbonylamino-5-(2-methoxyphenyl)-1,4,5,6-tetrahydropyrimidine;
2-methoxycarbonylamino-5-(4-methoxyphenyl)-1,4,5,6-tetrahydropyrimidine;
2-methoxycarbonylamino-5-(2-ethoxyphenyl)-1,4,5,6-tetrahydropyrimidine;
2-methoxycarbonylamino-5-(3-ethoxyphenyl)-1,4,5,6-tetrahydropyrimidine;
2-methoxycarbonylamino-5-(4-ethoxyphenyl)-1,4,5,6-tetrahydropyrimidine;
2-methoxycarbonylamino-5-(2-propoxyphenyl)-1,4,5,6-tetrahydropyrimidine;
2-methoxycarbonylamino-5-(3-propoxyphenyl)-1,4,5,6-tetrahydropyrimidine;
2-methoxycarbonylamino-5-(4-propoxyphenyl)-1,4,5,6-tetrahydropyrimidine;
2-methoxycarbonylamino-5-(4-butoxyphenyl)-1,4,5,6-tetrahydropyrimidine;
2-methoxycarbonylamino-5-(2-methylphenyl)-1,4,5,6-tetrahydropyrimidine;
2-methoxycarbonylamino-5-(3-methylphenyl)-1,4,5,6-tetrahydropyrimidine;
2-methoxycarbonylamino-5-(4-methylphenyl)-1,4,5,6-tetrahydropyrimidine;
2-methoxycarbonylamino-5-(2-ethylphenyl)-1,4,5,6-tetrahydropyrimidine;
2-methoxycarbonylamino-5-(3-ethylphenyl)-1,4,5,6-tetrahydropyrimidine;
2-methoxycarbonylamino-5-(4-ethylphenyl)-1,4,5,6-tetrahydropyrimidine;
2-methoxycarbonylamino-5-(2-isopropylphenyl)-1,4,5,6-tetrahydropyrimidine;
2-methoxycarbonylamino-5-(3-isopropylphenyl)-1,4,5,6-tetrahydropyrimidine;
2-methoxycarbonylamino-5-(4-isopropylphenyl)-1,4,5,6-tetrahydropyrimidine, ms 275 (M+);
2-methoxycarbonylamino-5-(2-trifluoromethylphenyl)-1,4,5,6-tetrahydropyrimidine;
2-methoxycarbonylamino-5-(3-trifluoromethylphenyl)-1,4,5,6-tetrahydropyrimidine;
2-methoxycarbonylamino-5-(4-trifluoromethylphenyl)-1,4,5,6-tetrahydropyrimidine;
2-methoxycarbonylamino-5-(2-methylthiophenyl)-1,4,5,6-tetrahydropyrimidine;
2-methoxycarbonylamino-5-(4-methylthiophenyl)-1,4,5,6-tetrahydropyrimidine;
2-methoxycarbonylamino-5-(2-ethylthiophenyl)-1,4,5,6-tetrahydropyrimidine;
2-methoxycarbonylamino-5-(4-ethylthiophenyl)-1,4,5,6-tetrahydropyrimidine;
2-methoxycarbonylamino-5-(2-butylthiophenyl)-1,4,5,6-tetrahydropyrimidine;
2-methoxycarbonylamino-5-(3-butylthiophenyl)-1,4,5,6-tetrahydropyrimidine;
2-methoxycarbonylamino-5-(4-methylsulfinylphenyl)-1,4,5,6-tetrahydropyrimidine;
2-methoxycarbonylamino-5-(4-ethylsulfonylphenyl)-1,4,5,6-tetrahydropyrimidine;
2-methoxycarbonylamino-5-(2,4-dimethoxyphenyl)-1,4,5,6-tetrahydropyrimidine;
2-methoxycarbonylamino-(2,6-diethoxyphenyl)-1,4,5,6-tetrahydropyrimidine;
2-methoxycarbonylamino-(3,5-diethylthiophenyl)-1,4,5,6-tetrahydropyrimidine;
2-methoxycarbonylamino-(2,6-dimethylsulfinylphenyl)-1,4,5,6-tetrahydropyrimidine;
2-methoxycarbonylamino-(2,6-dimethylsulfonylphenyl)-1,4,5,6-tetrahydropyrimidine; and the like.

C. Similarly, by following in principle the procedures of Part A of this example but substituting other bis-1,3(alkoxycarbonyl)-S-methylisothiourea or mono-1-alkoxycarbonyl-S-methylisothiourea such as 1-ethoxycarbonyl-S-methylisothiourea or 1-butoxycarbonyl-S-1-propoxycarbonyl-S-methylisothiourea for bis-1,3-(methoxycarbonyl)-S-methylisothiourea and a suitable 2-phenyl-1,3-propanediamine for 2-(methoxyphenyl)-1,3-propanediamine, other 2-alkoxycarbonylamino-5-phenyl-1,4,5,6-tetrahydropyrimidines are prepared such as 2-ethoxycarbonylamino-5-phenyl-1,4,5,6-tetrahydropyrimidine, mp 338°–343° C.;
2-isopropoxycarbonylamino-5-phenyl-1,4,5,6-tetrahydropyrimidine, mp 335°–342° C.; ms 261 (M+);
2-n-butoxycarbonylamino-5-phenyl-1,4,5,6-tetrahydropyrimidine;
2-n-propoxycarbonylamino-5-(3-bromophenyl)-1,4,5,6-tetrahydropyrimidine, mp 205°–206° C.;
2-i-propoxycarbonylamino-5-(2,6-dichlorophenyl)-1,4,5,6-tetrahydropyrimidine, mp 199°–201° C.; and the like.

EXAMPLE 6:
1-Alkyl-2-alkoxycarbonylamino-5-phenyl-1,4,5,6-tetrahydropyrimidines A. 1-Methyl-2-methoxycarbonylamino-5-phenyl-1,4,5,6-tetrahydropyrimidine To a solution of 1.5 g of the dihydrochloride of N-methyl-2-phenyl-1,3-propane diamine (prepared in accordance with Preparation F, Part A) in 200 ml of methanol is added first 0.68 g of sodium methoxide in a little methanol and then a solution of 1.3 g of 1,3-bis(methoxycarbonyl)-S-methylisothiourea in 200 ml of methanol. This mixture is allowed to stand at room temperature of 16 hours, is refluxed for 1 hour and is then concentrated to near dryness. The residue is dissolved in 50 ml of 3% hydrochloric acid and the resulting solution is washed with ether to remove non-basis impurities. The product is then precipitated by addition of saturated sodium bicarbonate. The solid is collected, washed with fresh water and dried under vacuum to give 0.99 g of product, mp 177–179. Recrystallization from ether gives 1-methyl-2-methyoxycarbonylamino-5-phenyl-1,4,5,6-tetrahydropyrimidine, mp 176°–177°.

B. In a similar manner by substituting other N-methyl-2-phenyl-1,3-propanediamines (prepared in accordance with Preparation F, Part B) for N-methyl-2-phenyl-1,3-propanediamine, other compounds of this invention are prepared such as 1-methyl-2-alkoxycarbonylamino-5-(2-fluorophenyl)-1,4,5,6-tetrahydropyrimidine;
1-methyl-2-alkoxycarbonylamino-5-(3-fluorophenyl)-1,4,5,6-tetrahydropyrimidine;
1-methyl-2-alkoxycarbonylamino-5-(4-fluorophenyl)-1,4,5,6-tetrahydropyrimidine;
1-methyl-2-alkoxycarbonylamino-5-(2-chlorophenyl)-1,4,5,6-tetrahydropyrimidine;
1-methyl-2-alkoxycarbonylamino-5-(3-chlorophenyl)-1,4,5,6-tetrahydropyrimidine;
1-methyl-2-alkoxycarbonylamino-5-(4-chlorophenyl)-1,4,5,6-tetrahydropyrimidine;
1-methyl-2-alkoxycarbonylamino-5-(3-bromophenyl)-1,4,5,6-tetrahydropyrimidine;
1-methyl-2-alkoxycarbonylamino-5-(4-iodophenyl)-1,4,5,6-tetrahydropyrimidine;
1-methyl-2-alkoxycarbonylamino-5-(2-hydroxyphenyl)-1,4,5,6-tetrahydropyrimidine;
1-methyl-2-alkoxycarbonylamino-5-(2-methoxyphenyl)-1,4,5,6-tetrahydropyrimidine;
1-methyl-2-alkoxycarbonylamino-5-(3-methoxyphenyl)-1,4,5,6-tetrahydropyrimidine;
1-methyl-2-alkoxycarbonylamino-5-(4-methoxyphenyl)-1,4,5,6-tetrahydropyrimidine;
1-methyl-2-alkoxycarbonylamino-5-(2-ethoxyphenyl)-1,4,5,6-tetrahydropyrimidine;
1-methyl-2-alkoxycarbonylamino-5-(3-isopropoxyphenyl)-1,4,5,6-tetrahydropyrimidine;
1-methyl-2-alkoxycarbonylamino-5-(4-benzyloxyphenyl)-1,4,5,6-tetrahydropyrimidine;
1-methyl-2-alkoxycarbonylamino-5-(4-t-butoxyphenyl)-1,4,5,6-tetrahydropyrimidine;
1-methyl-2-alkoxycarbonylamino-5-(2-methylphenyl)-1,4,5,6-tetrahydropyrimidine;
1-methyl-2-alkoxycarbonylamino-5-(3-methylphenyl)-1,4,5,6-tetrahydropyrimidine;
1-methyl-2-alkoxycarbonylamino-5-(4-methylphenyl)-1,4,5,6-tetrahydropyrimidine;
1-methyl-2-alkoxycarbonylamino-5-(2-ethylphenyl)-1,4,5,6-tetrahydropyrimidine;
1-methyl-2-alkoxycarbonylamino-5-(3-propylphenyl)-1,4,5,6-tetrahydropyrimidine;
1-methyl-2-alkoxycarbonylamino-5-(4-butylphenyl)-1,4,5,6-tetrahydropyrimidine;
1-methyl-2-alkoxycarbonylamino-5-(2-methylthiophenyl)-1,4,5,6-tetrahydropyrimidine;
1-methyl-2-alkoxycarbonylamino-5-(3-ethylthiophenyl)-1,4,5,6-tetrahydropyrimidine;
1-methyl-2-alkoxycarbonylamino-5-(4-butylthiophenyl)-1,4,5,6-tetrahydropyrimidine;
1-methyl-2-alkoxycarbonylamino-5-(4-methylsulfinylphenyl)-1,4,5,6-tetrahydropyrimidine;
1-methyl-2-alkoxycarbonylamino-5-(4-ethylsulfinylphenyl)-1,4,5,6-tetrahydropyrimidine;
1-methyl-2-alkoxycarbonylamino-5-(2,4-difluorophenyl)-1,4,5,6-tetrahydropyrimidine;
1-methyl-2-alkoxycarbonylamino-5-(2,6-dichlorophenyl)-1,4,5,6-tetrahydropyrimidine;
1-methyl-2-alkoxycarbonylamino-5-(3,5-dibromophenyl)-1,4,5,6-tetrahydropyrimidine;
1-methyl-2-alkoxycarbonylamino-5-(2,4-diiodophenyl)-1,4,5,6-tetrahydropyrimidine;
1-methyl-2-alkoxycarbonylamino-5-(2,6-dihydroxyphenyl)-1,4,5,6-tetrahydropyrimidine;
1-methyl-2-alkoxycarbonylamino-5-(2,4-dimethoxyphenyl)-1,4,5,6-tetrahydropyrimidine;
1-methyl-2-alkoxycarbonylamino-5-(3,5-dibutoxyphenyl)-1,4,5,6-tetrahydropyrimidine;
1-methyl-2-alkoxycarbonylamino-5-(2,6-dimethylphenyl)-1,4,5,6-tetrahydropyrimidine;
1-methyl-2-alkoxycarbonylamino-5-(2,4-dibutylphenyl)-1,4,5,6-tetrahydropyrimidine;
1-methyl-2-alkoxycarbonylamino-5-(2,6-dimethylthiophenyl)-1,4,5,6-tetrahydropyrimidine;
1-methyl-2-alkoxycarbonylamino-5-(2,4-dimethylsulfinylphenyl)-1,4,5,6-tetrahydropyrimidine;
1-methyl-2-alkoxycarbonylamino-5-(2,4-diethylsulfonylphenyl)-1,4,5,6-tetrahydropyrimidine; and the like.

EXAMPLE 7:
2-Amino-4-phenyl-1,4,5,6-tetrahydropyrimidines

A. A solution of 1.32 g of the dihydrochloride salt of 1-phenyl-1,3-propanediamine in a little water is made alkaline with excess of 30% sodium hydroxide and the free diamine is extracted 3 times with toluene. The extracts are combined, the toluene is evaporated and the residue is dissolved in 250 ml of methanol. A solution of 0.64 g of cyanogen bromide in methanol is added and the mixture is allowed to stand at room temperature for 5 hours and is then refluxed for 1 hour. The solvent is removed under vacuum to give an oil residue which is dissolved in 25 ml of isopropanol and the product crystallizes out to give 0.59 g of fine needles of 2-amino-4-phenyl-1,4,5,6-tetrahydropyrimidine, mp 192°–194°, hydrobromide.

B. In a similar manner, by substituting the appropriate 1-(substituted phenyl)-1,3-propanediamine prepared in accordance with Preparation E for phenyl-1,3-propanediamine, other compounds of this invention are prepared such as 2-amino-4-(2-chlorophenyl)-1,4,5,6-tetrahydropyrimidine;
2-amino-4-(3-chlorophenyl)-1,4,5,6-tetrahydropyrimidine;
2-amino-4-(4-chlorophenyl)-1,4,5,6-tetrahydropyrimidine;
2-amino-4-(2-fluorophenyl)-1,4,5,6-tetrahydropyrimidine;
2-amino-4-(3-fluorophenyl)-1,4,5,6-tetrahydropyrimidine;
2-amino-4-(4-fluorophenyl)-1,4,5,6-tetrahydropyrimidine;
2-amino-4-(2-bromophenyl)-1,4,5,6-tetrahydropyrimidine;
2-amino-4-(4-bromophenyl)-1,4,5,6-tetrahydropyrimidine;
2-amino-4-(2-iodophenyl)-1,4,5,6-tetrahydropyrimidine;
2-amino-4-(3-iodophenyl)-1,4,5,6-tetrahydropyrimidine;
2-amino-4-(4-iodophenyl)-1,4,5,6-tetrahydropyrimidine;
2-amino-4-(2,4-dichlorophenyl)-1,4,5,6-tetrahydropyrimidine;
2-amino-4-(3,5-dichlorophenyl)-1,4,5,6-tetrahydropyrimidine;
2-amino-4-(2,5-dichlorophenyl)-1,4,5,6-tetrahydropyrimidine;
2-amino-4-(2,6-dichlorophenyl)-1,4,5,6-tetrahydropyrimidine;
2-amino-4-(2,3-difluorophenyl)-1,4,5,6-tetrahydropyrimidine;
2-amino-4-(2,4-difluorophenyl)-1,4,5,6-tetrahydropyrimidine;
2-amino-4-(2,5-difluorophenyl)-1,4,5,6-tetrahydropyrimidine;
2-amino-4-(2,6-difluorophenyl)-1,4,5,6-tetrahydropyrimidine;
2-amino-4-(3,5-difluorophenyl)-1,4,5,6-tetrahydropyrimidine;
2-amino-4-(3,6-dibromophenyl)-1,4,5,6-tetrahydropyrimidine;
2-amino-4-(2,4-dibromophenyl)-1,4,5,6-tetrahydropyrimidine;
2-amino-4-(3,5-dibromophenyl)-1,4,5,6-tetrahydropyrimidine;
2-amino-4-(2,4-diiodophenyl)-1,4,5,6-tetrahydropyrimidine;
2-amino-4-(2,6-diiodophenyl)-1,4,5,6-tetrahydropyrimidine;
2-amino-4-(2-trifluoromethylphenyl)-1,4,5,6-tetrahydropyrimidine;
2-amino-4-(2-methoxyphenyl)-1,4,5,6-tetrahydropyrimidine;
2-amino-4-(3-methoxyphenyl)-1,4,5,6-tetrahydropyrimidine (hydrobromide salt), m.p. 189°–191° C.;
2-amino-4-(4-methoxyphenyl)-1,4,5,6-tetrahydropyrimidine;
2-amino-4-(2-ethoxyphenyl)-1,4,5,6-tetrahydropyrimidine;
2-amino-4-(3-ethoxyphenyl)-1,4,5,6-tetrahydropyrimidine;
2-amino-4-(4-ethoxyphenyl)-1,4,5,6-tetrahydropyrimidine;
2-amino-4-(2-propoxyphenyl)-1,4,5,6-tetrahydropyrimidine;
2-amino-4-(3-propoxyphenyl)-1,4,5,6-tetrahydropyrimidine;
2-amino-4-(4-propoxyphenyl)-1,4,5,6-tetrahydropyrimidine;
2-amino-4-(4-butoxyphenyl)-1,4,5,6-tetrahydropyrimidine;
2-amino-4-(4-methylphenyl)-1,4,5,6-tetrahydropyrimidine;
2-amino-4-(2-methylphenyl)-1,4,5,6-tetrahydropyrimidine;
2-amino-4-(3-methylphenyl)-1,4,5,6-tetrahydropyrimidine;
2-amino-4-(3-ethylphenyl)-1,4,5,6-tetrahydropyrimidine;
2-amino-4-(4-ethylphenyl)-1,4,5,6-tetrahydropyrimidine;
2-amino-4-(2-ethylphenyl)-1,4,5,6-tetrahydropyrimidine;
2-amino-4-(2-isopropylphenyl)-1,4,5,6-tetrahydropyrimidine;
2-amino-4-(3-isopropylphenyl)-1,4,5,6-tetrahydropyrimidine;
2-amino-4-(4-isopropylphenyl)-1,4,5,6-tetrahydropyrimidine;
2-amino-4-(2-trifluoromethylphenyl)-1,4,5,6-tetrahydropyrimidine;
2-amino-4-(3-trifluoromethylphenyl)-1,4,5,6-tetrahydropyrimidine;
2-amino-4-(4-trifluoromethylphenyl)-1,4,5,6-tetrahydropyrimidine;
2-amino-4-(2-methylthiophenyl)-1,4,5,6-tetrahydropyrimidine;
2-amino-4-(4-methylthiophenyl)-1,4,5,6-tetrahydropyrimidine;
2-amino-4-(2-ethylthiophenyl)-1,4,5,6-tetrahydropyrimidine;
2-amino-4-(4-ethylthiophenyl)-1,4,5,6-tetrahydropyrimidine;
2-amino-4-(2-butylthiophenyl)-1,4,5,6-tetrahydropyrimidine;
2-amino-4-(3-butylthiophenyl)-1,4,5,6-tetrahydropyrimidine;
2-amino-4-(4-methsulfinylphenyl)-1,4,5,6-tetrahydropyrimidine;
2-amino-4-(4-ethylsulfonylphenyl)-1,4,5,6-tetrahydropyrimidine;
2-amino-4-(2,4-dimethoxyphenyl)-1,4,5,6-tetrahydropyrimidine;
2-amino-4-(2,6-diethoxyphenyl)-1,4,5,6-tetrahydropyrimidine;
2-amino-4-(3,5-diethylthiophenyl)-1,4,5,6-tetrahydropyrimidine;
2-amino-4-(2,6-dimethylsulfinylphenyl)-1,4,5,6-tetrahydropyrimidine;
2-amino-4-(2,6-dimethylsulfonylphenyl)-1,4,5,6-tetrahydropyrimidine; and the like.

EXAMPLE 8:
2-Alkylcarbonylamino-4-phenyl-1,4,5,6-tetrahydropyrimidines

A. By following in principle the procedure of Example 3, Part A but substituting 2-amino-4-phenyl-1,4,5,6-tetrahydropyrimidine for 2-amino-5-phenyl-1,4,5,6-tetrahydropyrimidine, the corresponding 2-acetamido-4-phenyl-1,4,5,6-tetrahydropyrimidine is obtained.

B. Similarly, by following the procedure of Part A of this example but substituting tetrapropionylglycoluril or tetrabutyrylglycoluril for tetracetylglycoluril other amides of this invention are prepared such as 2-propionamido-4-phenyl-1,4,5,6-tetrahydropyrimidine or
2-butyramido-4-phenyl-1,4,5,6-tetrahydropyrimidine.

C. Similarly, by following the procedures of Parts A and B of this example, but substituting the other 2-amino-4-phenyl-1,4,5,6-tetrahydropyrimidine of Example 7, Part C for 2-amino-5-phenyl-1,4,5,6-tetrahydropyrimidine, the corresponding 2-acetamido, 2-propionamido or 2-butyramido-4-phenyl-1,4,5,6-tetrahydropyrimidines are prepared.

EXAMPLE 9:
2-Alkoxycarbonylamino-4-phenyl-1,4,5,6-tetrahydropyrimidines

A. 2-Methoxycarbonylamino-4-(4-fluorophenyl)-1,4,5,6-tetrahydropyrimidine

A solution of 0.93 g of 1-(4-fluorophenyl)1,3-propanediamine and 1.2 g of 1,3-bis(methoxycarbonyl)-S-methylisothiourea in 300 ml of methanol is refluxed for 2 hours and then concentrated to 25 ml to give crystals of 1.02 g of product having a m.p. 209°-214° C. Recrystallization of this product from 75 ml of methanol yields 0.8 g of 2-methoxycarbonylamino-4-(4-fluorophenyl)-1,4,5,6-tetrahydropyrimidine, m.p. 211°-212° C.

The hydrochloride salt is prepared from ethanol containing hydrogen chloride, m.p. 166°-168° C.

B. Similarly, by following in principle the process of Part A of this example but substituting other 1-(optionally substituted phenyl)-1,3-propanediamines prepared according to the process of Preparation G, Part 2 for 1-(3-methoxyphenyl)-1,3-propanediamine, other compounds of this invention are prepared such as
2-methoxycarbonylamino-4-phenyl-1,4,5,6-tetrahydropyrimidine, m.p. 186°-190° C.;
2-methoxycarbonylamino-4-(2-chlorophenyl)-1,4,5,6-tetrahydropyrimidine;
2-methoxycarbonylamino-4-(3-chlorophenyl)-1,4,5,6-tetrahydropyrimidine;
2-methoxycarbonylamino-4-(4-chlorophenyl)-1,4,5,6-tetrahydropyrimidine;
2-methoxycarbonylamino-4-(2-fluorophenyl)-1,4,5,6-tetrahydropyrimidine;
2-methoxycarbonylamino-4-(3-fluorophenyl)-1,4,5,6-tetrahydropyrimidine;
2-methoxycarbonylamino-4-(2-bromophenyl)-1,4,5,6-tetrahydropyrimidine;
2-methoxycarbonylamino-4-(3-bromophenyl)-1,4,5,6-tetrahydropyrimidine;
2-methoxycarbonylamino-4-(4-bromophenyl)-1,4,5,6-tetrahydropyrimidine;
2-methoxycarbonylamino-4-(2-iodophenyl)-1,4,5,6-tetrahydropyrimidine;
2-methoxycarbonylamino-4-(3-iodophenyl)-1,4,5,6-tetrahydropyrimidine;
2-methoxycarbonylamino-4-(4-iodophenyl)-1,4,5,6-tetrahydropyrimidine;
2-methoxycarbonylamino-4-(2,4-dichlorophenyl)-1,4,5,6-tetrahydropyrimidine;
2-methoxycarbonylamino-4-(3,5-dichlorophenyl)-1,4,5,6-tetrahydropyrimidine;
2-methoxycarbonylamino-4-(2,5-dichlorophenyl)-1,4,5,6-tetrahydropyrimidine;
2-methoxycarbonylamino-4-(2,6-dichlorophenyl)-1,4,5,6-tetrahydropyrimidine;
2-methoxycarbonylamino-4-(2,3-difluorophenyl)-1,4,5,6-tetrahydropyrimidine;
2-methoxycarbonylamino-4-(2,4-difluorophenyl)-1,4,5,6-tetrahydropyrimidine;
2-methoxycarbonylamino-4-(2,5-difluorophenyl)-1,4,5,6-tetrahydropyrimidine;
2-methoxycarbonylamino-4-(2,6-difluorophenyl)-1,4,5,6-tetrahydropyrimidine; 2-methoxycarbonylamino-4-(3,5-difluorophenyl)-1,4,5,6-tetrahydropyrimidine;
2-methoxycarbonylamino-4-(3,6-dibromophenyl)-1,4,5,6-tetrahydropyrimidine;
2-methoxycarbonylamino-4-(2,4-dibromophenyl)-1,4,5,6-tetrahydropyrimidine;
2-methoxycarbonylamino-4-(3,5-dibromophenyl)-1,4,5,6-tetrahydropyrimidine;
2-methoxycarbonylamino-4-(2,4-diiodophenyl)-1,4,5,6-tetrahydropyrimidine;
2-methoxycarbonylamino-4-(2,6-diiodophenyl)-1,4,5,6-tetrahydropyrimidine;
2-methoxycarbonylamino-4-(2-methoxyphenyl)-1,4,5,6-tetrahydropyrimidine;
2-methoxycarbonylamino-4-(4-methoxyphenyl)-1,4,5,6-tetrahydropyrimidine;
2-methoxycarbonylamino-4-(2-ethoxyphenyl)-1,4,5,6-tetrahydropyrimidine;
2-methoxycarbonylamino-4-(3-ethoxyphenyl)-1,4,5,6-tetrahydropyrimidine;
2-methoxycarbonylamino-4-(4-ethoxyphenyl)-1,4,5,6-tetrahydropyrimidine;
2-methoxycarbonylamino-4-(2-propoxyphenyl)-1,4,5,6-tetrahydropyrimidine;
2-methoxycarbonylamino-4-(3-propoxyphenyl)-1,4,5,6-tetrahydropyrimidine;
2-methoxycarbonylamino-4-(4-propoxyphenyl)-1,4,5,6-tetrahydropyrimidine;
2-methoxycarbonylamino-4-(4-butoxyphenyl)-1,4,5,6-tetrahydropyrimidine;
2-methoxycarbonylamino-4-(2-methylphenyl)-1,4,5,6-tetrahydropyrimidine;
2-methoxycarbonylamino-4-(3-methylphenyl)-1,4,5,6-tetrahydropyrimidine;
2-methoxycarbonylamino-4-(4-methylphenyl)-1,4,5,6-tetrahydropyrimidine, m.p. 198°-200° C.;
2-methoxycarbonylamino-4-(2-ethylphenyl)-1,4,5,6-tetrahydropyrimidine;
2-methoxycarbonylamino-4-(3-ethylphenyl)-1,4,5,6-tetrahydropyrimidine;
2-methoxycarbonylamino-4-(4-ethylphenyl)-1,4,5,6-tetrahydropyrimidine;
2-methoxycarbonylamino-4-(2-isopropylphenyl)-1,4,5,6-tetrahydropyrimidine;
2-methoxycarbonylamino-4-(3-isopropylphenyl)-1,4,5,6-tetrahydropyrimidine;
2-methoxycarbonylamino-4-(4-isopropylphenyl)-1,4,5,6-tetrahydropyrimidine;
2-methoxycarbonylamino-4-(2-trifluoromethylphenyl)-1,4,5,6-tetrahydropyrimidine, m.p. 195°-197° C.;

2-methoxycarbonylamino-4-(3-trifluoromethylphenyl)-1,4,5,6-tetrahydropyrimidine;
2-methoxycarbonylamino-4-(4-trifluoromethylphenyl)-1,4,5,6-tetrahydropyrimidine;
2-methoxycarbonylamino-4-(2-methylthiophenyl)-1,4,5,6-tetrahydropyrimidine;
2-methoxycarbonylamino-4-(4-methylthiophenyl)-1,4,5,6-tetrahydropyrimidine;
2-methoxycarbonylamino-4-(2-ethylthiophenyl)-1,4,5,6-tetrahydropyrimidine;
2-methoxycarbonylamino-4-(4-ethylthiophenyl)-1,4,5,6-tetrahydropyrimidine;
2-methoxycarbonylamino-4-(2-butylthiophenyl)-1,4,5,6-tetrahydropyrimidine;
2-methoxycarbonylamino-4-(3-butylthiophenyl)-1,4,5,6-tetrahydropyrimidine;
2-methoxycarbonylamino-4-(4-methsulfinylphenyl)-1,4,5,6-tetrahydropyrimidine;
2-methoxycarbonylamino-4-(4-ethylsulfonylphenyl)-1,4,5,6-tetrahydropyrimidine;
2-methoxycarbonylamino-4-(2,4-dimethoxyphenyl)-1,4,5,6-tetrahydropyrimidine;
2-methoxycarbonylamino-4-(2,6-diethoxyphenyl)-1,4,5,6-tetrahydropyrimidine;
2-methoxycarbonylamino-4-(3,5-diethylthiophenyl)-1,4,5,6-tetrahydropyrimidine;
2-methoxycarbonylamino-4-(2,6-dimethylsulfinylphenyl)-1,4,5,6-tetrahydropyrimidine;
2-methoxycarbonylamino-4-(2,6-dimethylsulfonylphenyl)-1,4,5,6-tetrahydropyrimidine; and the like.

C. Similarly, by following in principle the procedures of Part A of this example but substituting other bis-1,3(alkoxycarbonyl)-S-methylisothiourea or mono-1-alkoxycarbonyl-S-methylisothiourea such as 1-ethoxycarbonyl-S-methylisothiourea, 1-propoxycarbonyl-S-methylisothiourea or 1-butoxycarbonyl-S-methylisothiourea for bis-1,3-(methoxycarbonyl)-S-methylisothiourea and a suitable 1-phenyl-1,3-propanediamine for 1-(4-fluorophenyl)-1,3-propanediamine, other 2-alkoxycarbonylamino4-phenyl-1,4,5,6-tetrahydropyrimidines are prepared such as
2-ethoxycarbonylamino-4-phenyl-1,4,5,6-tetrahydropyrimidine;
2-isopropoxycarbonylamino-4-phenyl-1,4,5,6-tetrahydropyrimidine;
2-n-propoxycarbonylamino-4-phenyl-1,4,5,6-tetrahydropyrimidine, m.p. 134°–137° C.;
2-n-butoxycarbonylamino-4-phenyl-1,4,5,6-tetrahydropyrimidine;
2-n-propoxycarbonylamino-4-(3-bromophenyl)-1,4,5,6-tetrahydropyrimidine;
2-i-propoxycarbonylamino-4-(2,6-dichlorophenyl)-1,4,5,6-tetrahydropyrimidine; and the like.

The subject matter claimed is:

1. A compound selected from the group of compounds represented by the formula

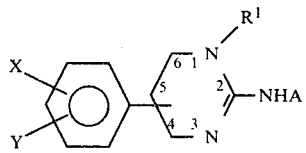
(I)

wherein
A is H or

where R is alkyl of one through six carbon atoms;
X is hydrogen, fluoro, chloro, bromo, iodo, hydroxy, alkoxy of one through four carbon atoms, benzyloxy, alkyl of one through four carbon atoms, alkylthio of one through four carbon atoms, alkylsulfinyl of one through four carbon atoms, alkylsulfonyl of one through four carbon atoms or trifluoromethyl; and
Y is hydrogen or is the same as X; and
$R^1$ is hydrogen or alkyl of one through four carbon atoms; the phenyl substituent carrying the X and Y is at the 4- or 5-position of the tetrahydropyrimidine ring when $R^1$ is hydrogen or is at the 5-position when $R^1$ is alkyl; and the pharmaceutically acceptable salts thereof.

2. The compound of claim 1 where A is H and the moiety represented by the formula

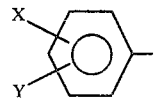

is at the 5-position of the 1,4,5,6-tetrahydropyrimidine ring.

3. The compound of claim 2 wherein $R^1$ is hydrogen.

4. The compound of claim 3 wherein X and Y are each hydrogen, namely 2-amino-5-phenyl-1,4,5,6-tetrahydropyrimidine.

5. The compound of claim 3 wherein X and Y are each chloro.

6. The compound of claim 5 wherein X and Y are at the 3,4-positions, namely 2-amino-5-(3,4-dichlorophenyl)-1,4,5,6-tetrahydropyrimidine.

7. The compound of claim 5 wherein X and Y are at the 2,4-positions, namely 2-amino-5-(2,4-dichlorophenyl)-1,4,5,6-tetrahydropyrimidine.

8. The compound of claim 5 wherein X and Y are at the 2,6-positions, namely 2-amino-5-(2,6-dichlorophenyl)-1,4,5,6-tetrahydropyrimidine.

9. The compound of claim 3 wherein X is hydrogen and Y is fluoro.

10. The compound of claim 9 wherein Y is 4-fluoro, namely 2-amino-5-(4-fluorophenyl)-1,4,5,6-tetrahydropyrimidine.

11. The compound of claim 3 wherein X is hydrogen and Y is 3-bromo, namely 2-amino-5-(3-bromophenyl)-1,4,5,6-tetrahydropyrimidine.

12. The compound of claim 3 wherein X is hydrogen and Y is 3-chloro, namely 2-amino-5-(3-chlorophenyl)-1,4,5,6-tetrahydropyrimidine.

13. The compound of claim 3 wherein X is hydrogen and Y is 3-methoxy, namely 2-amino-5-(3-methoxyphenyl)-1,4,5,6-tetrahydropyrimidine.

14. The compound of claim 1 where A is hydrogen, the moiety represented by the formula

is at the 4-position of the 1,4,5,6-tetrahydropyrimidine ring and R¹ is hydrogen.

15. The compound of claim 14 wherein X and Y are both hydrogen, namely 2-amino-4-phenyl-1,4,5,6-tetrahydropyrimidine.

16. The compound of claim 14 wherein X and Y are both chloro.

17. The compound of claim 14 wherein X is hydrogen and Y is 2-trifluoromethyl, namely 2-amino-4-(2-trifluoromethylphenyl)-1,4,5,6-tetrahydropyrimidine.

18. The compound of claim 14 wherein X is hydrogen and Y is 3-methoxy, namely 2-amino-4-(3-methoxyphenyl)-1,4,5,6-tetrahydropyrimidine.

19. The compound of claim 14 wherein X is hydrogen and Y is 4-methyl, namely 2-amino-4-(4-methylphenyl)-1,4,5,6-tetrahydropyrimidine.

20. The compound of claim 14 wherein X is hydrogen and Y is 4-fluoro, namely 2-amino-4-4-(4-fluorophenyl)-1,4,5,6-tetrahydropyrimidine.

21. The compound of claim 1 wherein A is

R¹ is hydrogen and the moiety represented by the formula.

is at the 5 position on the 1,4,5,6-tetrahydropyrimidine ring.

22. The compound of claim 21 wherein Y is hydrogen.

23. The compound of claim 22 wherein X is hydrogen.

24. The compound of claim 23 wherein R is methyl, namely 2-methoxycarbonylamino-5-phenyl-1,4,5,6-tetrahydropyrimidine.

25. The hydrochloride salt of the compound of claim 24.

26. The compound of claim 23 wherein R is ethyl, namely 2-ethoxycarbonylamino-5-phenyl-1,4,5,6-tetrahydropyrimidine.

27. The compound of claim 23 wherein R is isopropyl, namely 2-isopropoxycarbonylamino-5-phenyl-1,4,5,6-tetrahydropyrimidine.

28. The compound of claim 22 wherein X is chloro.

29. The compound of claim 28 wherein X is 2-chloro and R is methyl, namely 2-methoxycarbonylamino-5-(2-chlorophenyl)-1,4,5,6-tetrahydropyrimidine.

30. The compound of claim 22 wherein X is bromo.

31. The compound of claim 30 wherein X is 3-bromo and R is methyl, namely 2-methoxycarbonylamino-5-(3-bromophenyl)-1,4,5,6-tetrahydropyrimidine.

32. The compound of claim 30 wherein X is 3-bromo and R is n-propyl, namely 2-n-propoxycarbonylamino-5-(3-bromophenyl)-1,4,5,6-tetrahydropyrimidine.

33. The compound of claim 22 wherein X is methoxy.

34. The compound of claim 33 wherein X is 3-methoxy and R is methyl, namely 2-methoxycarbonylamino-5-(3-methoxyphenyl)-1,4,5,6-tetrahydropyrimidine.

35. The compound of claim 22 wherein X is fluoro.

36. The compound of claim 35 wherein X is 4-fluoro and R is methyl, namely 2-methoxycarbonylamino-5-(4-fluorophenyl)-1,4,5,6-tetrahydropyrimidine.

37. The compound of claim 22 wherein X is alkyl of one through three carbon atoms.

38. The compound of claim 37 wherein X is 4-isopropyl and R is methyl, namely 2-methoxycarbonylamino-5-(4-isopropylphenyl)-1,4,5,6-tetrahydropyrimidine.

39. The compound of claim 21 wherein X and Y are both chloro.

40. The compound of claim 39 wherein R is methyl.

41. The compound of claim 40 wherein X and Y are at the 3,4-positions, namely 2-methoxycarbonylamino-5-(3,4-dichlorophenyl)-1,4,5,6-tetrahydropyrimidine.

42. The compound of claim 40 wherein X and Y are at the 2,4-positions, namely 2-methoxycarbonylamino-5-(2,4-dichlorophenyl)-1,4,5,6-tetrahydropyrimidine.

43. The compound of claim 40 wherein X and Y are at the 2,6-positions, namely 2-methoxycarbonylamino-5-(2,6-dichlorophenyl)-1,4,5,6-tetrahydropyrimidine.

44. The compound of claim 39 wherein R is isopropyl.

45. The compound of claim 44 wherein X and Y are at the 2,6-positions, namely 2-isopropoxycarbonylamino-5-(2,6-dichlorophenyl)-1,4,5,6-tetrahydropyrimidine.

46. The compound of claim 1 wherein A is

R¹ is hydrogen and the moiety represented by the formula

is at the 4-position of the 1,4,5,6-tetrahydropyrimidine ring.

47. The compound of claim 21 wherein Y is hydrogen.

48. The compound of claim 47 wherein X is hydrogen.

49. The compound of claim 48 where R is methyl, namely 2-methoxycarbonylamino-4-phenyl-1,4,5,6-tetraretrahydropyrimidine.

50. The compound of claim 48 wherein R is n-propyl, namely 2-n-propoxy-carbonylamino-4-phenyl-1,4,5,6-tetrahydropyrimidine.

51. The compound of claim 48 wherein X is trifluoromethyl.

52. The compound of claim 51 wherein X is 2-trifluoromethyl and R is methyl, namely 2-methoxycarbonylamino-4-(2-trifluoromethylphenyl)-1,4,5,6-tetrahydropyrimidine.

53. The compound of claim 47 wherein X is methoxy.

54. The compound of claim 53 wherein X is 3-methoxy and R is methyl, namely 3-methoxycarbonylamino-4-(3-methoxyphenyl)-1,4,5,6-tetrahydropyrimidine.

55. The compound of claim 47 wherein X is methyl.

56. The compound of claim 55 wherein X is 4-methyl and R is methyl, namely 4-methoxycarbonylamino-4-(4-methylphenyl)-1,4,5,6-tetrahydropyrimidine.

57. The compound of claim 47 wherein X is fluoro.

58. The compound of claim 57 wherein X is 4-fluoro and R is methyl, namely 2-methoxycarbonylamino-4-(4-fluorophenyl)-1,4,5,6-tetrahydropyrimidine.

59. A pharmaceutical composition which is useful for treating, palliating or preventing undesirable conditions in mammals involving the central nervous system and which comprises a therapeutically effective amount of a compound of claim 1 and at least one pharmaceutically acceptable excipient.

* * * * *